(12) United States Patent
Motai et al.

(10) Patent No.: US 9,198,686 B2
(45) Date of Patent: Dec. 1, 2015

(54) MEDICAL INSTRUMENT

(75) Inventors: Kosuke Motai, Tokyo (JP); Masatoshi Sato, Tokyo (JP); Kunihide Kaji, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 110 days.

(21) Appl. No.: 13/445,198

(22) Filed: Apr. 12, 2012

(65) Prior Publication Data

US 2012/0289985 A1  Nov. 15, 2012

Related U.S. Application Data

(63) Continuation of application No. PCT/JP2011/066551, filed on Jul. 21, 2011.

(60) Provisional application No. 61/369,151, filed on Jul. 30, 2010.

(51) Int. Cl.
*A61B 17/34* (2006.01)
*A61B 17/3205* (2006.01)
*A61B 10/02* (2006.01)
*A61B 17/08* (2006.01)
*A61B 17/00* (2006.01)
*A61B 17/30* (2006.01)

(52) U.S. Cl.
CPC ....... *A61B 17/32053* (2013.01); *A61B 10/0233* (2013.01); *A61B 17/083* (2013.01); *A61B 2017/00269* (2013.01); *A61B 2017/00358* (2013.01); *A61B 2017/306* (2013.01); *A61B 2017/3405* (2013.01)

(58) Field of Classification Search
CPC ........... A61B 10/0233; A61B 10/0266; A61B 17/32053
See application file for complete search history.

(56) References Cited

U.S. PATENT DOCUMENTS

| 4,456,010 A | * | 6/1984 | Reimels et al. | 606/173 |
| 5,112,299 A | * | 5/1992 | Pascaloff | 604/22 |
| 5,133,360 A | * | 7/1992 | Spears | 600/567 |
| 5,346,497 A | * | 9/1994 | Simon et al. | 606/107 |
| 5,573,008 A | * | 11/1996 | Robinson et al. | 600/567 |

(Continued)

FOREIGN PATENT DOCUMENTS

| JP | UM-A-64-006915 | 1/1989 |
| JP | A-05-317324 | 12/1993 |

(Continued)

OTHER PUBLICATIONS

International Search Report dated Oct. 18, 2011 issued in PCT/JP2011/066551.

*Primary Examiner* — Jonathan W Miles
*Assistant Examiner* — Todd J Scherbel
(74) *Attorney, Agent, or Firm* — Scully, Scott, Murphy & Presser, PC

(57) ABSTRACT

A medical instrument includes a medical needle configured to puncture a tissue, and a tissue-supporting member configured to be inserted into the lumen of the medical needle and supports the tissue. The medical needle includes an insertion portion that has a longitudinal axis, a lumen that is formed along the direction of the longitudinal axis of the insertion portion, an opening portion that is formed at the distal end of the insertion portion while being connected to the lumen, and a puncturing portion that is formed in the periphery of the opening portion and has a pair of projections sharply protruding in a direction extending toward the distal end from the proximal end of the insertion portion.

9 Claims, 26 Drawing Sheets

(56) References Cited

U.S. PATENT DOCUMENTS

| | | | | |
|---|---|---|---|---|
| 5,863,294 | A * | 1/1999 | Alden | 606/167 |
| 6,238,355 | B1 * | 5/2001 | Daum | 600/567 |
| 6,419,684 | B1 * | 7/2002 | Heisler et al. | 606/170 |
| 7,008,381 | B2 * | 3/2006 | Janssens | 600/564 |
| 2008/0039880 | A1 * | 2/2008 | Nohilly et al. | 606/167 |
| 2008/0208214 | A1 | 8/2008 | Sato et al. | |

FOREIGN PATENT DOCUMENTS

| | | |
|---|---|---|
| JP | A-07-100140 | 4/1995 |
| JP | A-08-206118 | 8/1996 |
| JP | A-11-226024 | 8/1999 |
| JP | T-2002-538922 | 11/2002 |
| JP | A-2005-073798 | 3/2005 |
| JP | A-2008-183020 | 8/2008 |

* cited by examiner

MEDICAL INSTRUMENT

The present application is a continuing application based on PCT Patent Application No. PCT/JP2011/066551, whose priority is claimed on U.S. Patent Provisional Application No. 61/369,151 applied in the US on Jul. 30, 2010. The contents of both the PCT application and the US Patent Application are incorporated herein by reference.

BACKGROUND OF THE INVENTION

1. Technical Field

The present invention relates to a medical instrument including a medical needle that is used for puncturing tissues.

2. Background Art

Conventionally, medical needles have been widely used for various purposes such as tissue biopsy and drainage of pus performed by puncturing tissues. For general medical needles, the end of a tubular member formed of a metal is obliquely cut such that the end slants to the axis, whereby a sharp distal end is formed in the needles.

Although the general medical needle has one sharp distal end, as a medical needle for tissue biopsy, a needle called a Franseen needle in which three sharp distal ends are formed is also known.

SUMMARY OF THE INVENTION

According to a first aspect of the present invention, a medical instrument includes a medical needle that punctures a tissue, and a tissue-supporting portion that is inserted into the lumen of the medical needle and supports the tissue. The medical needle includes an insertion portion that has a longitudinal axis, a lumen that is formed along the direction of the longitudinal axis of the insertion portion, an opening portion that is formed at a distal end of the insertion portion while being connected to the lumen, and a puncturing portion that is formed in the periphery of the opening portion and has a pair of projections sharply protruding in a direction extending toward the distal end from a proximal end of the insertion portion.

The projection of the medical needle that is included in the medical instrument according to the first aspect of the present invention may have an edge portion that is formed so as to form an acute angle to a tangent line with respect to the lumen in at least one position of the end portion in the circumferential direction.

The outer circumferential surface of the distal end portion of the projection of the medical needle that is included in the medical instrument according to the first aspect of the present invention may be processed such that the distal end portion becomes thinned toward the distal end.

The medical needle that is included in the medical instrument according to the first aspect of the present invention may include two members each of which has one projection, and the members may face each other so as to form the lumen and be supported by a supporting member so as to be able to move relative to each other in the axis direction.

In the medical needle that is included in the medical instrument according to the first aspect of the present invention, at least a portion of the lumen may be formed more thinly compared to other portions so as to form a small inner diameter portion.

The medical needle that is included in the medical instrument according to the first aspect of the present invention may have a tube that is connected to a suction source.

The medical needle that is included in the medical instrument according to the first aspect of the present invention may have one projection at the distal end that is made to puncture a tissue and further include a tissue-penetrating portion that is inserted into the lumen.

The tissue-supporting member of the medical instrument according to the first aspect of the present invention may have two projections at the distal end that is made to puncture the tissue.

The tissue-supporting member of the medical instrument according to the first aspect of the present invention may be a pair of forceps that includes a pair of forceps blades which can be opened and closed.

BEST MODE FOR CARRYING OUT THE INVENTION (First Embodiment)

Hereinbelow, the respective embodiments of the present invention will be described with reference to FIGS. 1A to 7.

Figure 1A:
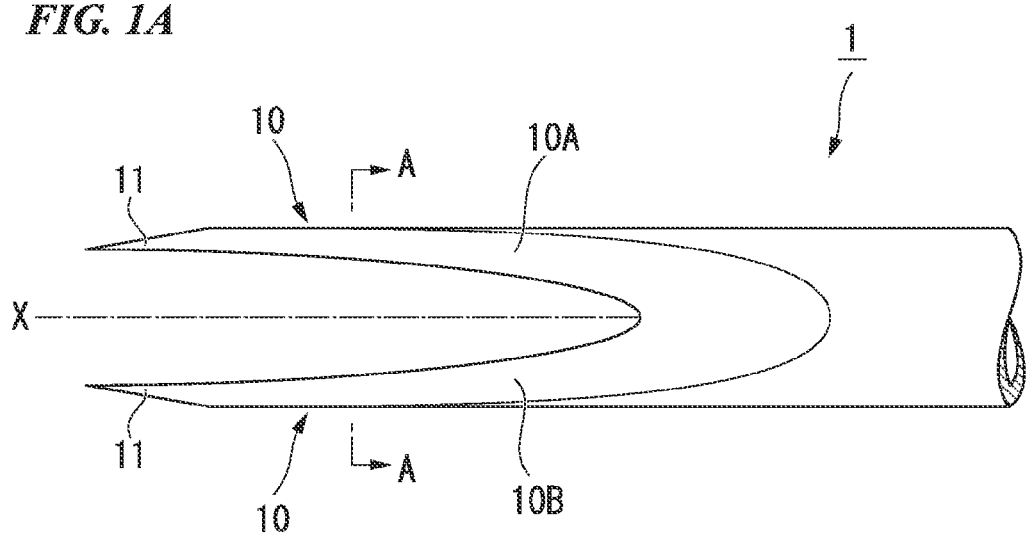
FIG. 1A is an enlarged right side view of the distal end portion of the medical needle of a first embodiment of the present invention.
Figure 1B:
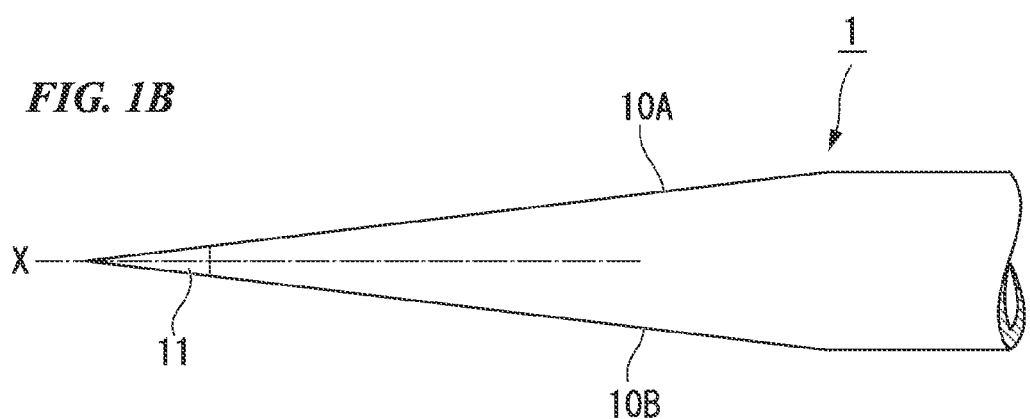
FIG. 1B is an enlarged bottom view of the distal end portion of the medical needle of the first embodiment of the present invention.
Figure 1C:
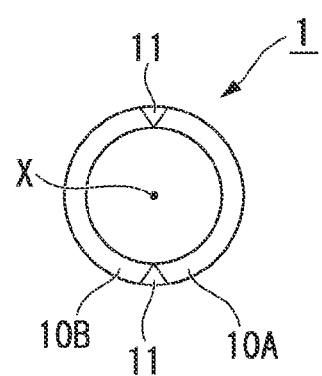
FIG. 1C is an enlarged front view of the distal end portion of the medical needle of the first embodiment of the present invention.
Figure 1D:
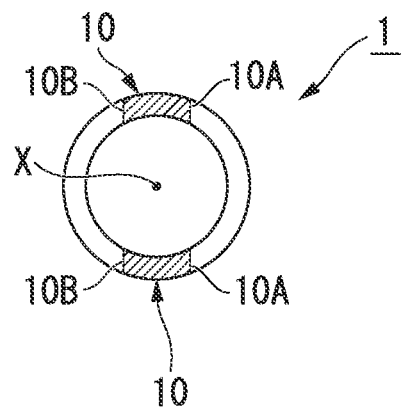
FIG. 1D is an enlarged cross-sectional view taken along the line A-A of FIG. 1A of the distal end portion of the medical needle of the first embodiment of the present invention.

FIGS. 1A to 1D are partially enlarged views showing the distal end portion of the medical needle included in the medical instrument of the first embodiment of the present invention. FIG. 1A is a right side view of a medical needle 1 of the present embodiment. FIG. 1B is a bottom view of the medical needle 1. FIG. 1C is a front view of the medical needle 1. FIG. 1D is a cross-sectional view taken along the line A-A of FIG. 1A. The medical needle 1 is formed in a tube shape having a lumen. The medical needle 1 includes two sharp projections 10 at the distal end. As shown in FIGS. 1A and 1B, the two projections 10 are formed by cutting out one end (distal end) of a tubular member formed of a metal such as stainless steel from both sides in the radial direction that face each other while interposing an axis X so as to form slopes 10A and 10B that slant to the axis X and become close to the outer circumferential surface toward the other end (proximal end) from the distal end. As shown in FIGS. 1C and 1D, in the front view of the medical needle 1, the slopes 10A and 10B are positioned at both sides in the circumferential direction of the respective projections 10 and function as cutting blade portions described later (hereinbelow, the slopes 10A and 10B are also called cutting blade portions 10A and 10B respectively). The cutting blade portions positioned at both sides in the circumferential direction of the respective projections 10 are approximately parallel to each other in a cross-section perpendicular to the axis X in the projection 10.

The area of the distal end of the respective projections 10 is formed so as to become thinned toward the distal end and configure a puncturing portion 11 that is formed sharply so as to be easily made to penetrate a tissue.

The length of the medical needle 1 is appropriately set according to the target tissue, the procedure, or the like. An operation portion for facilitating forward and backward operations (movement in the axis X direction) or a turning operation (described later) of the medical needle 1 may be appropriately provided to the proximal end of the medical needle 1.

Figure 2:
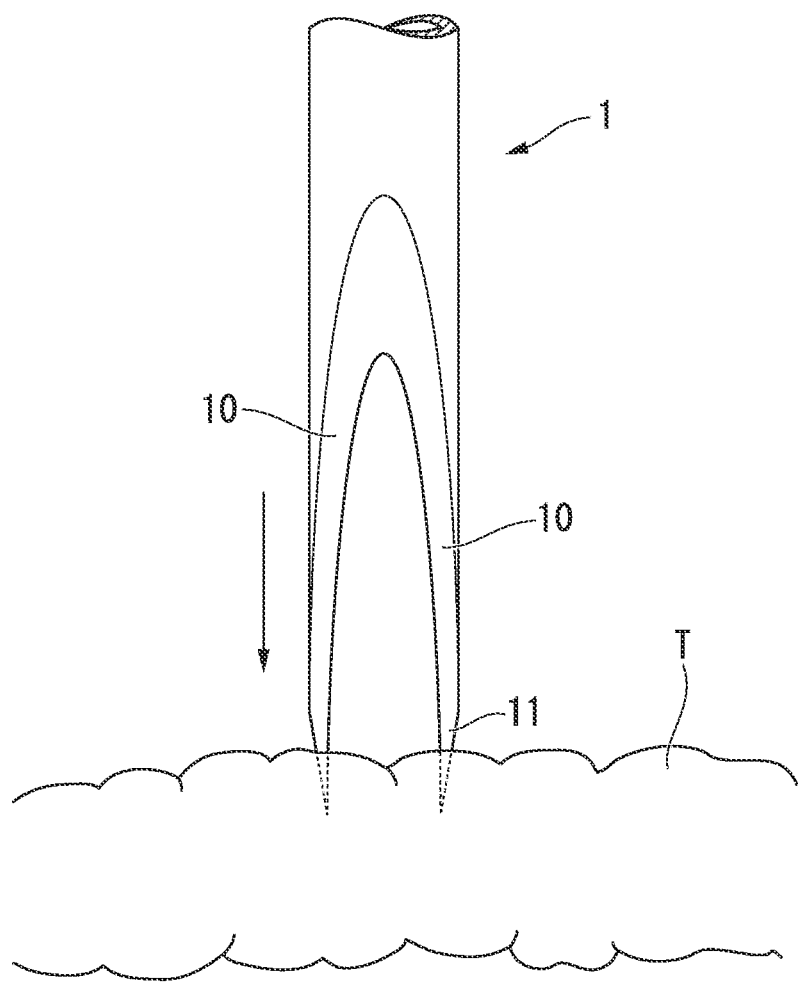
FIG. 2 is a view showing an operation at the time of using the medical needle of the first embodiment of the present invention.
Figure 3A:
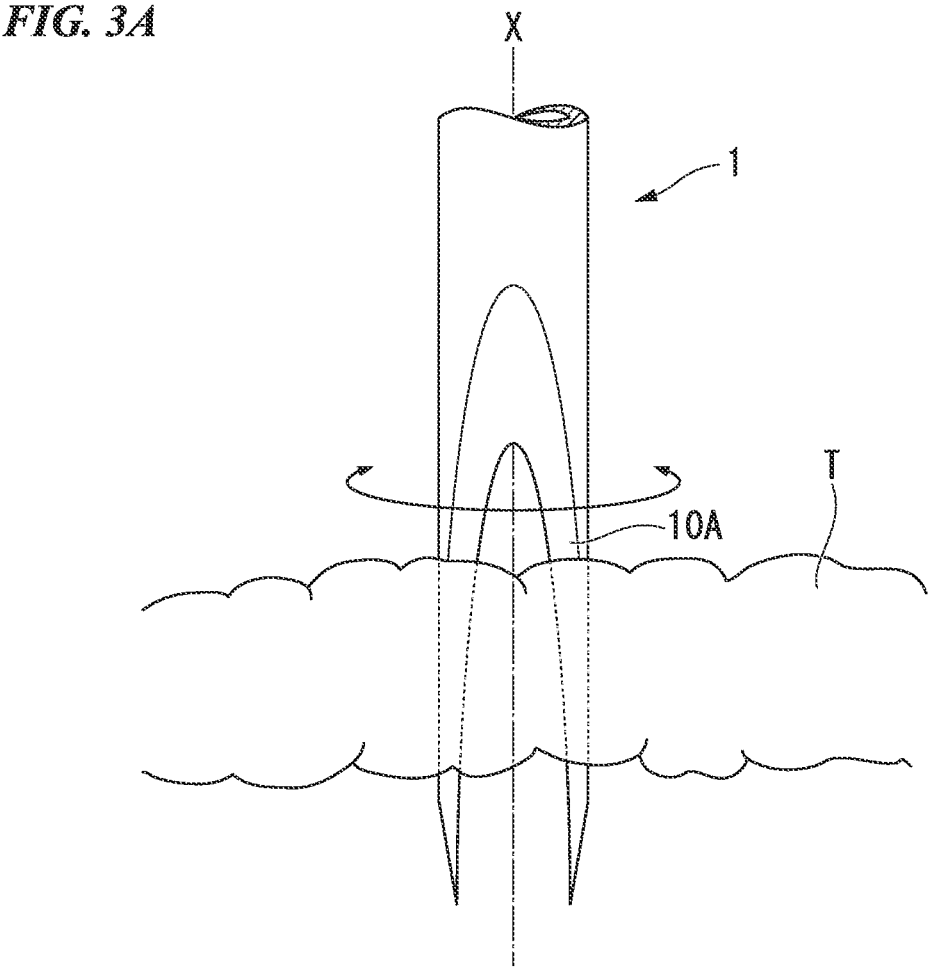
FIG. 3A is a view showing an operation at the time of using the medical needle of the first embodiment of the present invention.

The operations at the time of using the medical needle 1 according to the present embodiment that is configured as above will be described. The medical needle 1 is used for forming a hole that looks like a circle in a plan view by excising a portion of a tissue so as to hollow out the tissue. When a hole is formed, first, an operator makes the two projections 10 of the medical needle 1 puncture a tissue T in which the hole is to be formed, as shown in FIG. 2. When the puncturing portion 11 is made to puncture to a predetermined depth, the operator operates the proximal end portion or the like of the medical needle 1 and turns the distal end of the medical needle 1 including the projections 10 on the axis X as shown in FIG. 3A. Basically, the predetermined depth is determined appropriately according to the shape of the hole to be formed. When a hole penetrating the tissue T is formed, the puncturing portion 11 is punctured until the puncturing portion 11 protrudes from the other side of the tissue as shown in FIG. 3A. When a bottomed hole is formed in the tissue T, the puncturing depth is set such that the distal end of the projection 10 is positioned inside the tissue T as shown in FIG. 2.

Figure 3B:
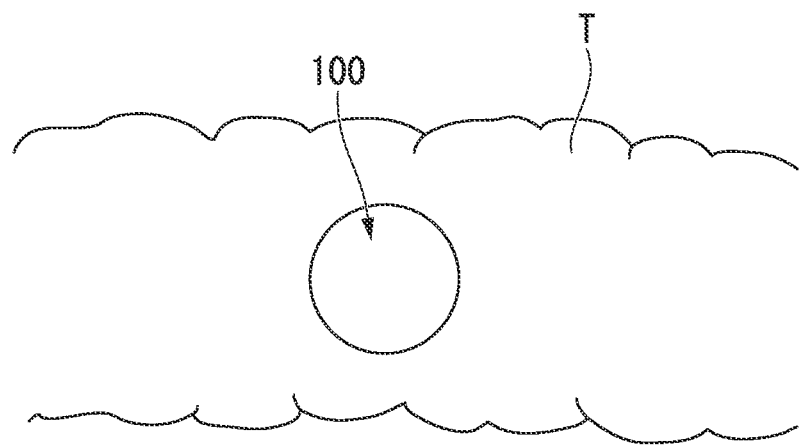
FIG. 3B is a view showing an operation at the time of using the medical needle of the first embodiment of the present invention.

When the distal end is turned around the axis X, one of the cutting blade portions 10A and 10B positioned at both sides in the circumferential direction in the respective projections 10 is pressed on the tissue T, whereby the tissue T is lacerated. If the distal end is made a half turn or more and preferably turns once or more, the tissue is excised in a circular shape along the locus of the cutting blade portion, whereby a hole 100 is formed as shown in FIG. 3B. When the excision ends, the operator pulls the medical needle 1 out of the tissue T. Thereafter, if necessary, the operator provides hemostasis to the formed hole 100 or recovers the excised tissue, thereby completing the procedure.

According to the medical needle 1 of the present embodiment, there are two projections 10. Therefore, by making the projections 10 puncture the tissue T, the tissue T is held so as not to turn relative to the medical needle 1. Consequently, after being made to puncture the tissue T, the projections 10 are turned on the axis X, whereby the cutting blade portions keep cutting the tissue T stably and excise a portion of the tissue T so as to hollow out the tissue T. In this manner, the approximately circular hole 100 can be easily formed.

The puncturing portion 11 provided to the distal end of the projection 10 is formed so as to become thinned toward the distal end. Therefore, the outer circumferential surface of the puncturing portion 11 becomes close to the axis X toward the distal end. As a result, when the medical needle 1 is used by being inserted into a channel of an endoscope, an issue that the inner wall of the channel is damaged since the projection 10 is caught in the channel or the like can be suitably prevented.

Figure 4:
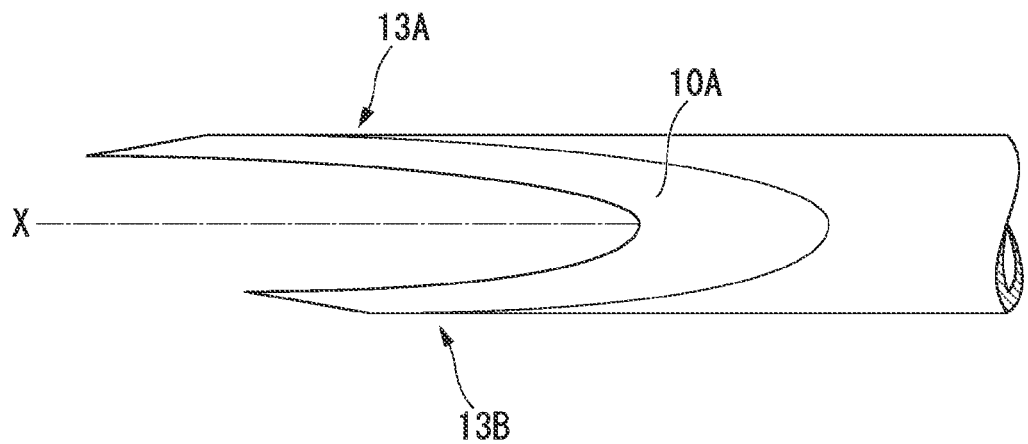
FIG. 4 is a partially enlarged view showing the distal end portion of the medical needle of a modified example of the first embodiment of the present invention.
Figure 5:
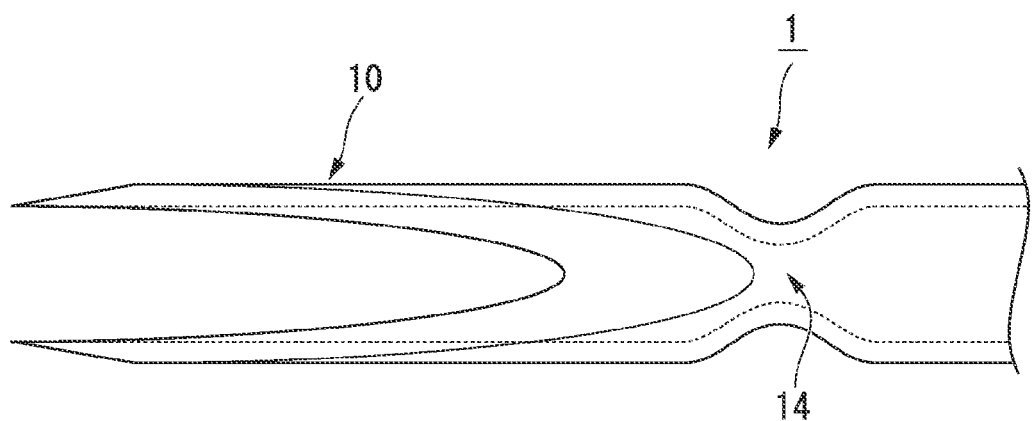
FIG. 5 is a partially enlarged view showing the distal end portion of the medical needle of a modified example of the first embodiment of the present invention.

In the medical needle 1 of the present embodiment, for example, by varying the inclination angle of the slopes 10A and 10B based on the axis X as a boundary, projections 13A and 13B having a different length may be formed as the modified example shown in FIG. 4. In this case, since the projections can be made to puncture the tissue one by one, it is possible to reduce force required for puncturing. In addition, as the modified example shown in FIG. 5, by causing a portion of the outer circumferential surface of the distal end from the projection 10 to protrude toward the lumen, a small inner diameter portion 14 having a thinned lumen may be formed. In this case, a tissue that enters the lumen of the medical needle 1 when the projection 10 is punctured does not easily pass through the small inner diameter portion 14, whereby it is possible to prevent the medical needle 1 from excessively puncturing the tissue.

Figure 6:
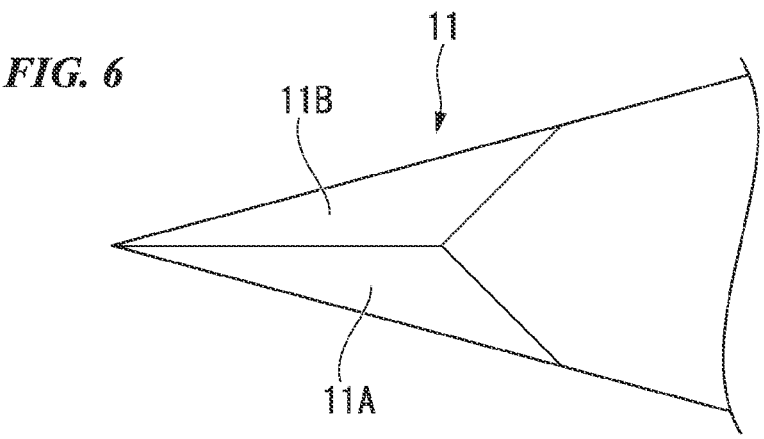
FIG. 6 is a partially enlarged view showing the distal end portion of the medical needle of a modified example of the first embodiment of the present invention.
Figure 7:
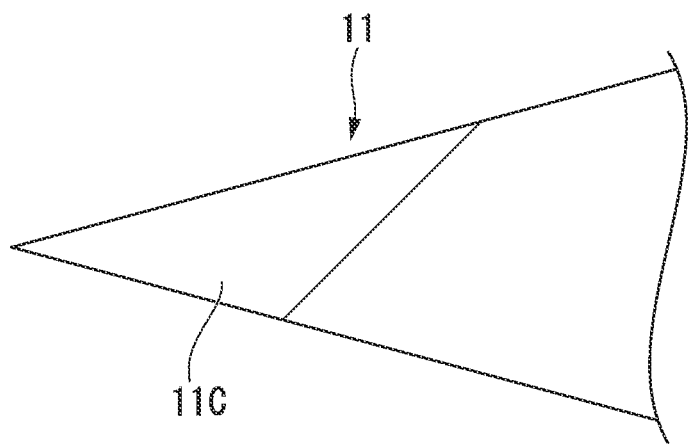
FIG. 7 is a partially enlarged view showing the distal end portion of the medical needle of a modified example of the first embodiment of the present invention.

In addition, as the puncturing portion 11, as shown by being enlarged in FIG. 6, slopes 11A and 11B may be formed so as to become thinned toward both sides in the circumferential direction instead of being formed in the shape of the present embodiment. Alternatively, as shown in FIG. 7, the puncturing portion 11 may be formed so as to have a slope 11C only in one side in the circumferential direction. At this time, the slope 11C may be formed in any side. In this case, even in the turning operation performed after puncturing, if the needle is turned in the direction in which the slope 11C is formed, it is possible to suitably lacerate the tissue. Consequently, in the turning operation, the slope 11C becomes an aid for lacerating the tissue, so it is possible to smoothly excise the tissue.

(Second Embodiment)

The second embodiment of the present invention will be described with reference to FIGS. 8A to 10B. A medical needle 21 of the present embodiment is different from the medical needle 1 of the first embodiment in the shape of the cutting blade portion. In the following description, configurations similar to those already described are marked with the same symbols so as to omit repeated descriptions.

Figure 8A:
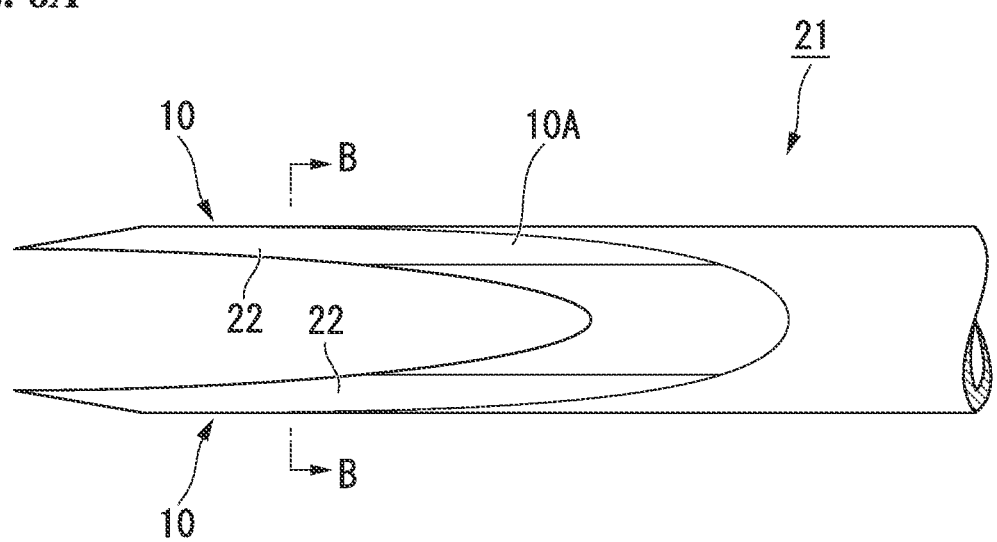
FIG. 8A is an enlarged right side view of the distal end portion of the medical needle of a second embodiment of the present invention.
Figure 8B:
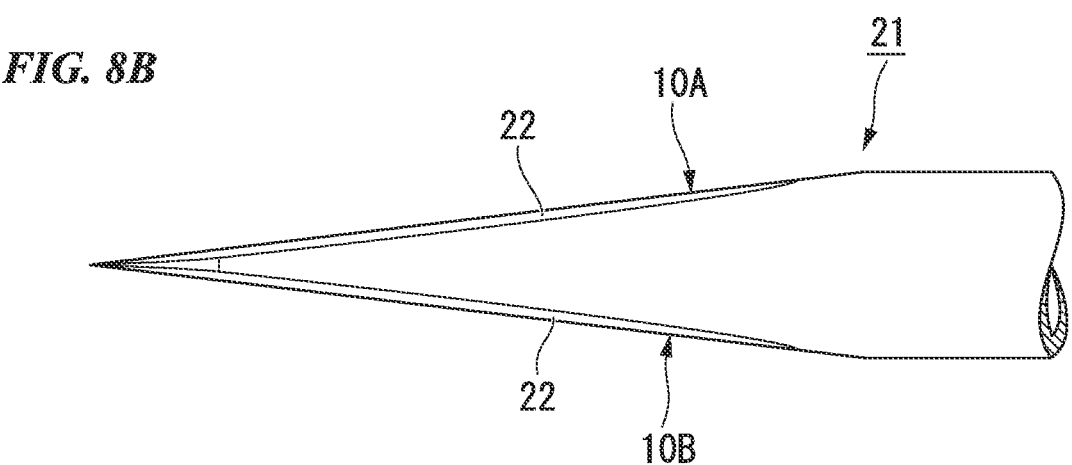
FIG. 8B is an enlarged bottom view of the distal end portion of the medical needle of the second embodiment of the present invention.
Figure 8C:
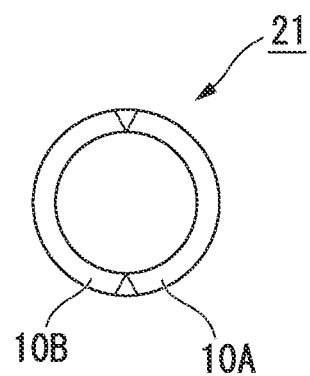
FIG. 8C is an enlarged front view of the distal end portion of the medical needle of the second embodiment of the present invention.
Figure 8D:
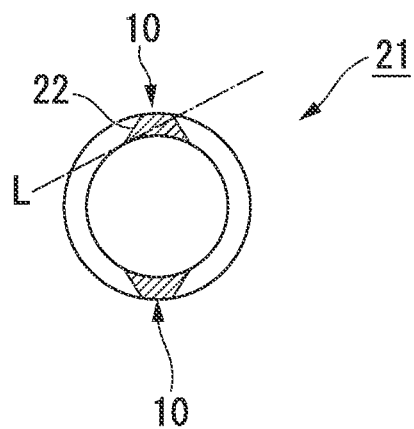
FIG. 8D is an enlarged cross-sectional view taken along the line B-B of the distal end portion of the medical needle of the second embodiment of the present invention.

FIG. 8A to 8D are partially enlarged views showing the distal end portion of the medical needle 21. FIG. 8A is a right side view of the medical needle 21. FIG. 8B is a bottom view of the medical needle 21. FIG. 8C is a front view of the medical needle 21. FIG. 8D is a cross-sectional view taken along the line B-B of FIG. 8A. In the medical needle 21, a portion of the slopes 10A and 10B forming the two projections 10 has been processed, and the outer circumferential surface of each projection 10 is formed such that the thickness of the projection 10 is reduced toward both sides in the circumferential direction. Consequently, as shown in FIG. 8D, each projection 10 has an edge portion 22 that forms a further acute angle to a tangent line L with respect to the inner wall of the tubular medical needle 21 in both sides in the circumferential direction.

Figure 9:
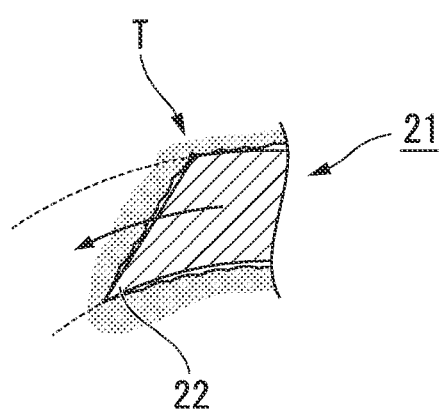
FIG. 9 is a view showing an operation at the time of using the medical needle of the second embodiment of the present invention.

If the turning operation described above is performed using the medical needle 21 of the present embodiment, the edge portion 22 first contacts the tissue T among the cutting blade portions and lacerates the tissue T as shown in FIG. 9. Accordingly, compared to the medical needle 1 of the first embodiment in which all cutting blade portions come into surface-contact with the tissue in the turning operation, the medical needle 21 more reliably lacerates the tissue, and it is possible to suitably excise the tissue with less force.

Figure 10A:
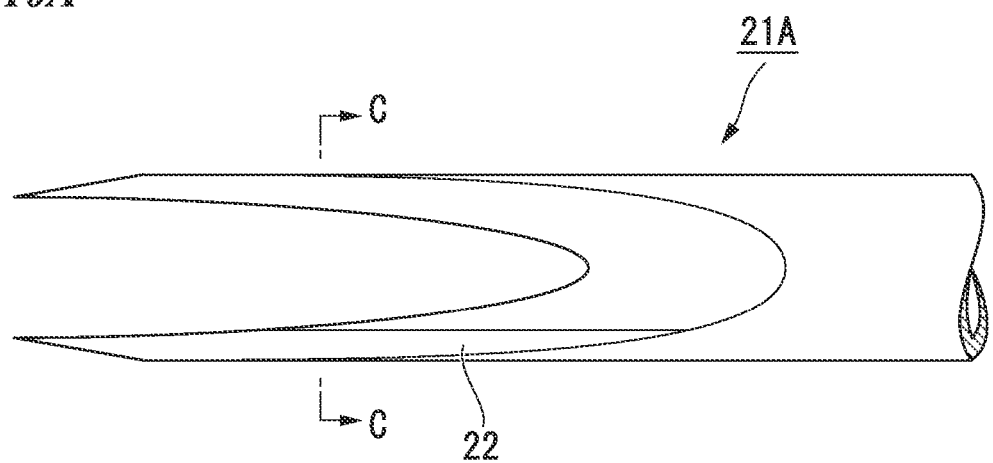
FIG. 10A is a partially enlarged view showing the distal end portion of the medical needle of a modified example of the second embodiment of the present invention.
Figure 10B:
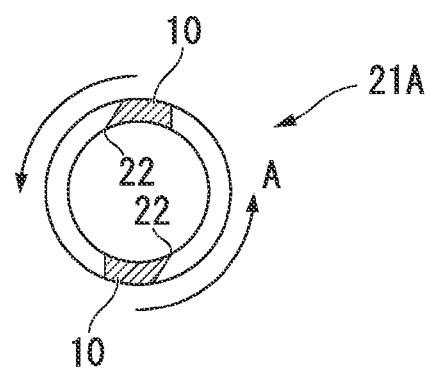
FIG. 10B is a cross-sectional view taken along the line C-C of FIG. 10A.

In the present embodiment, an example in which the edge portions are formed in both sides in the circumferential direction of the projection has been described. However, instead of this, as the medical needle 21A of the modified example shown in FIGS. 10A and 10B, the edge portion may be formed only in the surface of one cutting blade in the circumferential direction of the projection 10. FIG. 10B is a cross-sectional view taken along the line C-C of FIG. 10A. When the medical needle 21A is turned in the direction of the arrow A shown in FIG. 10B, the medical needle 21A can suitably excise the tissue. If the medical needle 21A is turned in a direction opposite to the arrow A, the tissue is not easily cut, so it is possible to prevent the tissue from being cut by a false operation.

The shapes of the various modified examples described in the first embodiment may be combined with the medical needle of the present embodiment. For example, if the puncturing portion 11 is formed so as to have the slopes 11A and 11B, all of the slopes 11A and 11B and the edge portion 22 are placed in the same plane, so an edge portion continues to the distal end of the projection.

Figure 11A:
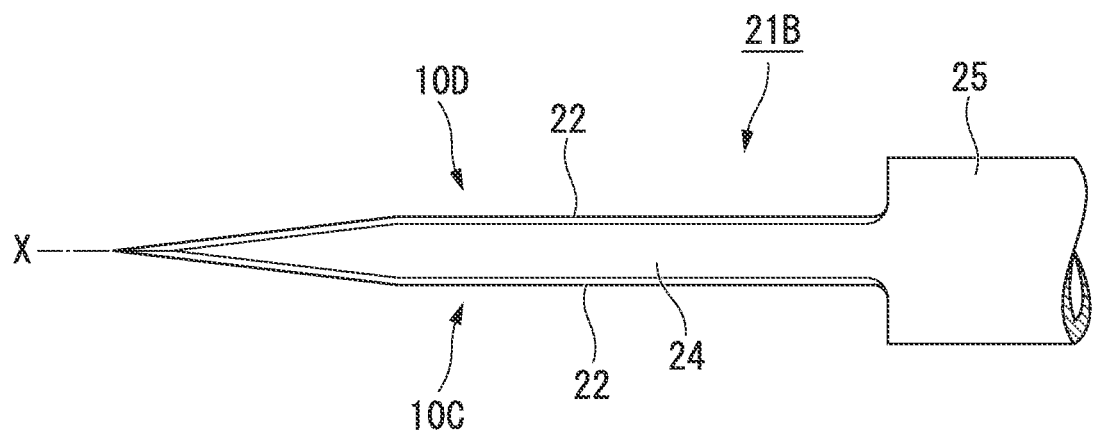
FIG. 11A is a partially enlarged view showing the distal end portion of the medical needle of another modified example of the second embodiment of the present invention.
Figure 11B:
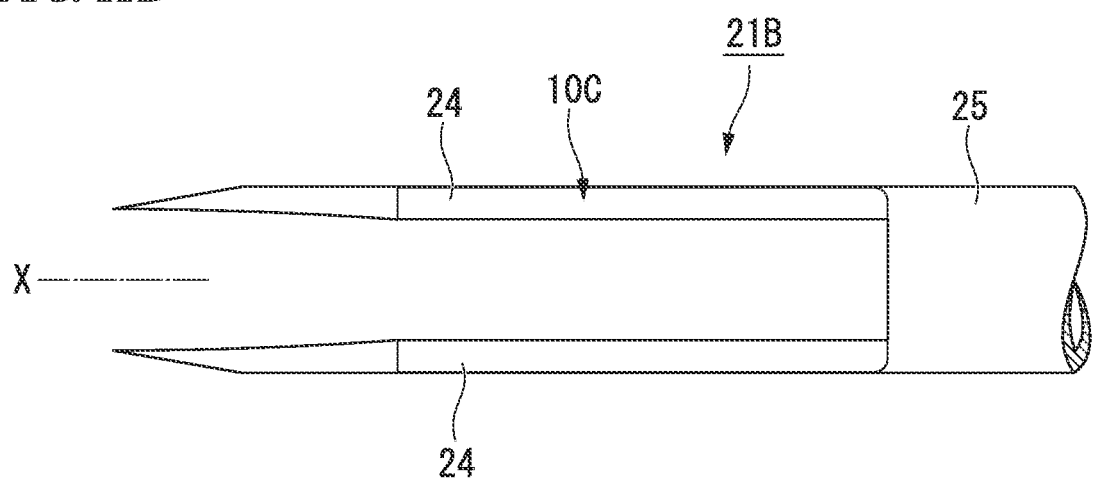
FIG. 11B is a partially enlarged view showing the distal end portion of the medical needle of the other modified example of the second embodiment of the present invention.

In addition, as a medical needle 21B of the modified example shown in FIGS. 11A and 11B, the cutting blade portion may be formed by the surfaces 10C and 10D parallel to the axis X instead of being formed by a slope.

In this case, a process for forming the edge portion 22 in the cutting blade portion becomes easy. In addition, since the dimension of each projection 24 in the circumferential direction becomes consistent except for the portion near the distal end, an outer circumferential surface 25 that covers the whole circumference of the medical needle 21B in the proximal end portion of the projection 24 functions as a stopper. That is, the medical needle may relatively be made to smoothly puncture the tissue to the proximal end portion of the projection 24, but it is not easy to make the outer circumferential surface 25 puncture the tissue since the outer circumferential surface covers the whole circumference abruptly in the proximal end portion. Accordingly, it is possible to prevent the medical needle from deeply puncturing the tissue accidently due to a false operation or the like. The shape of this type of projection may be applied to the medical needle of the first embodiment.

Figure 12:
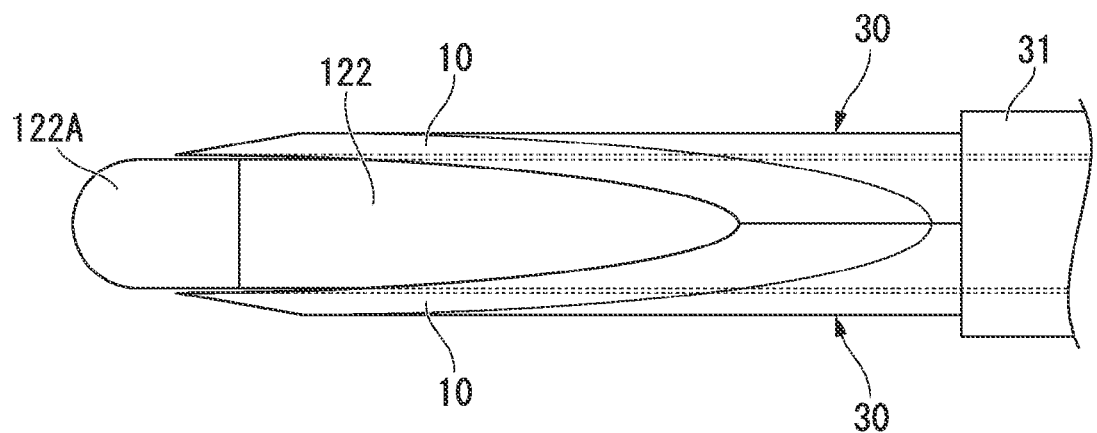
FIG. 12 is a partially enlarged view showing the distal end portion of the medical needle of a modified example of the second embodiment of the present invention.

In the medical needle of the present invention, two half pipe-like members 30 in which one projection 10 is formed in each of these members may be prepared and caused to face each other to form a tubular shape, and a tube 31 formed of a resin or the like may support the members 30 such these members can move relative to each other in the axis direction as shown in FIG. 12. In this case, by causing one of the members 30 to protrude relative to the other member, it is possible to make the projection portions 10 puncture the tissue one by one. Consequently, it is possible to more easily perform a procedure with reducing force required for puncturing.

(Third Embodiment)

Next, the third embodiment of the present invention will be described. In the present embodiment, the medical instrument including the medical needle described above will be described.

Figure 13A:
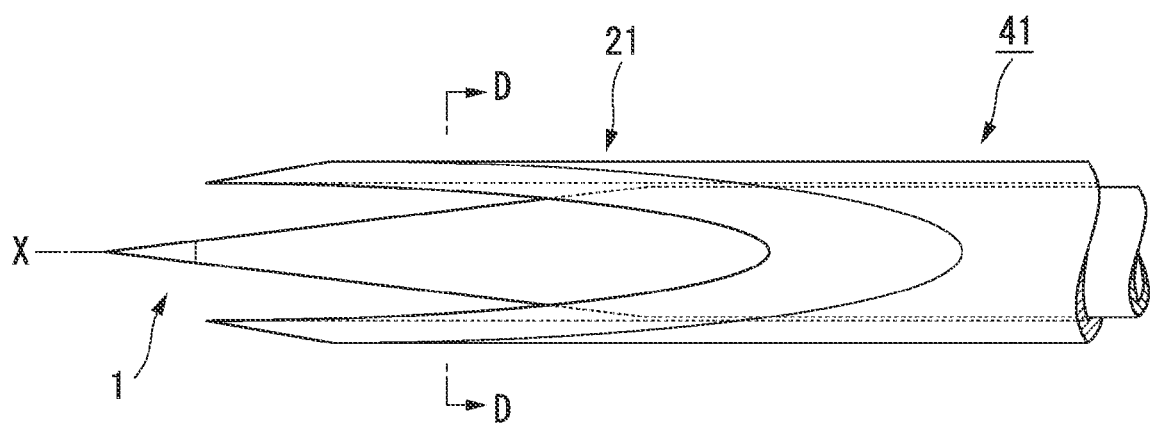
FIG. 13A is an enlarged view showing the right side of the distal end portion of the medical instrument of a third embodiment of the present invention.
Figure 13B:
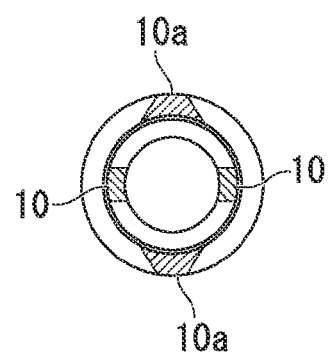
FIG. 13B is a cross-sectional view taken along the line D-D of FIG. 13A.

FIGS. 13A and 13B are partially enlarged views showing the distal end of the medical instrument 41 of the present embodiment. FIG. 13A is a right side view of the medical instrument 41. FIG. 13B is a cross-sectional view taken along the line D-D of FIG. 13A. The medical instrument 41 includes the medical needle 21 (cutting blade member) of the second embodiment and the medical needle 1 (tissue-supporting member) inserted into the medical needle 21.

The medical needle 21 (hereinbelow, also referred to as a "cutting blade member 21") as a cutting blade member and the medical needle 1 (hereinbelow, also referred to as a "tissue-supporting member 1") as a tissue-supporting member are arranged so as to be able to move relative to each other in the axis X direction or turn relative to each other on the axis X.

The operation at the time of using the medical instrument 41 of the present embodiment configured as above will be described.

Figure 14:
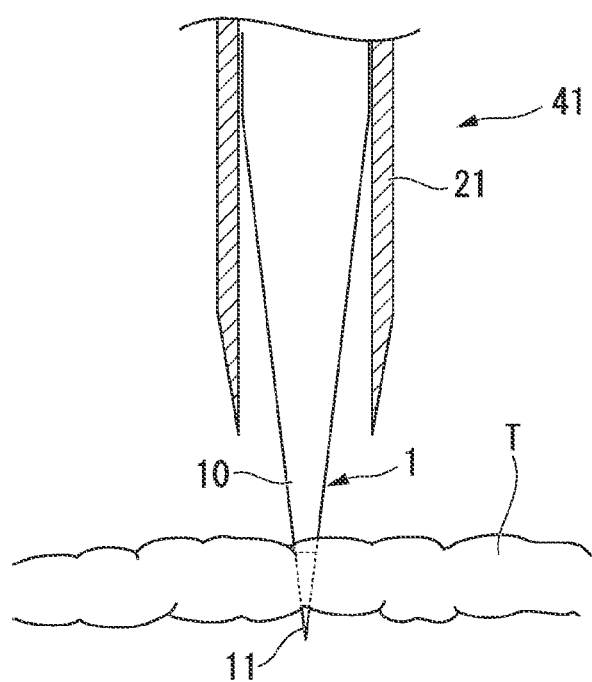
FIG. 14 is a view showing an operation at the time of using the medical instrument of the third embodiment of the present invention.

First, an operator delivers the medical instrument 41 to a position near a target tissue. The operator causes the distal end portion of the tissue-supporting member 1 to protrude from the cutting blade member 21, and makes the puncturing portion 11 puncture the tissue T as shown in FIG. 14. The two projections 10 of the tissue-supporting member 1 are made to puncture the tissue T, whereby the tissue T is supported at two points by the tissue-supporting member 1.

Figure 15:
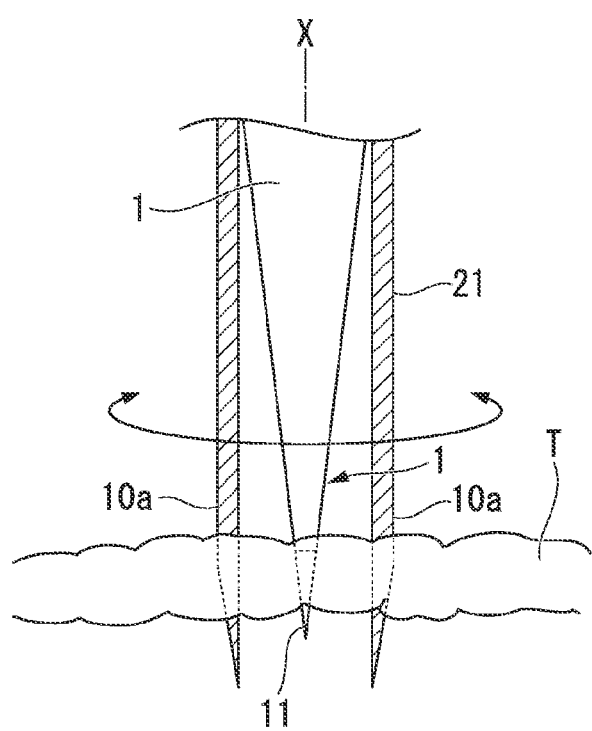
FIG. 15 is a view showing an operation at the time of using the medical instrument of the third embodiment of the present invention.

Subsequently, the operator causes the cutting blade member 21 to move forward with respect to the tissue-supporting member 1, thereby making the two projections 10a puncture the tissue T. In addition, as shown in FIG. 15, while holding the tissue-supporting member 1, the operator turns the cutting blade member 21 on the axis X. At this time, in the tissue T, a site excised when a hole is formed is supported at two points by the tissue-supporting member 1. Accordingly, this site is prevented from turning along with the turning operation of the cutting blade member 21 and suitably lacerated by the edge portion of the cutting blade member 21.

According to the medical instrument 41 of the present embodiment, it is possible to excise the tissue by turning the cutting blade member 21 while holding the tissue T with the tissue-supporting member 1 inserted into the cutting blade member 21. Consequently, it is possible to suitably and easily perform a procedure forming a hole in the tissue. In addition, when plural layers such as adjacent luminal tissues are excised (described later in detail), by turning the cutting blade member 21 in a state where the tissue-supporting member 1 supports the plural layers by penetrating the layers for example, the plural layers can be excised at one time.

In the medical instrument according to the embodiment of the present invention, both of the cutting blade member and the tissue supporting member can employ various configurations.

As the cutting blade member, any member can be used as long as the member is the medical needle according to the embodiment of the present invention. However, in the medical instrument 41, the function of the cutting blade member is specialized for lacerating a tissue by the turning operation, so the cutting blade member preferably has projections including edge portions similarly to the medical needle 21 of the second embodiment.

When the medical needle according to the embodiment of the present invention is used as the tissue-supporting member, it is preferable that the tissue-supporting member can puncture and support the tissue at two points. Accordingly, for example, a member specialized for improving a puncturing property that may have projections not including edge portions may be used. In addition, for example, a member may be used which is formed by dividing two medical needles used in the related art that include only one sharp distal end by planes parallel to the axis, causing half pipe-like members having the sharp distal end to face each other, and holding those members together by using the tube 31 or the like similarly to the medical needle shown in FIG. 12.

Figure 16:
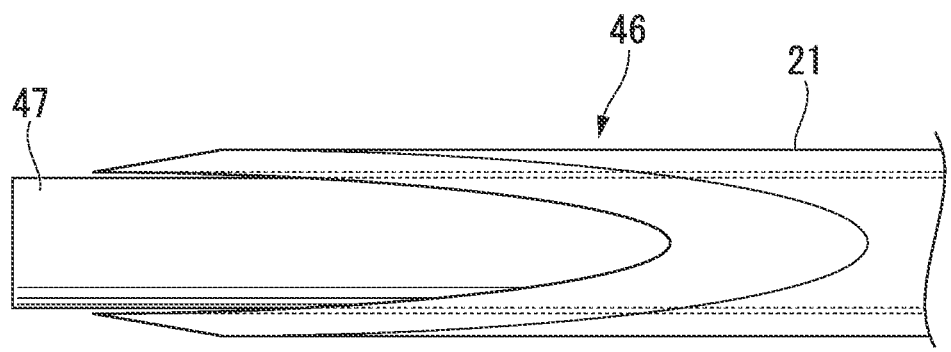
FIG. 16 is a partially enlarged view showing the distal end portion of the medical instrument of a modified example of the third embodiment of the present invention.
Figure 17:
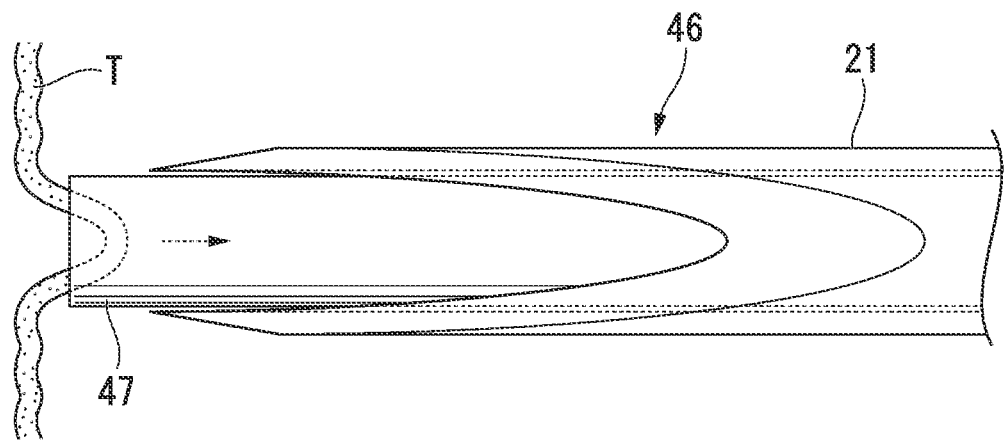
FIG. 17 is a view showing an operation at the time of using the medical instrument shown in FIG. 16.

It is preferable that the tissue-supporting member can inhibit a tissue from turning along with the turning operation of the cutting blade member, so the tissue-supporting member may not be made to puncture the tissue. In a medical instrument 46 of the modified example shown in FIG. 16, a tube 47 inserted into the cutting blade member 21 functions as the tissue-supporting member. The tube 47 is connected to a suction source not shown in the drawing. When the suction source is operated, since the tube 47 holds the tissue T as shown in FIG. 17, it is possible to prevent the tissue T from turning along with the turning operation of the cutting blade member 21.

Figure 18:
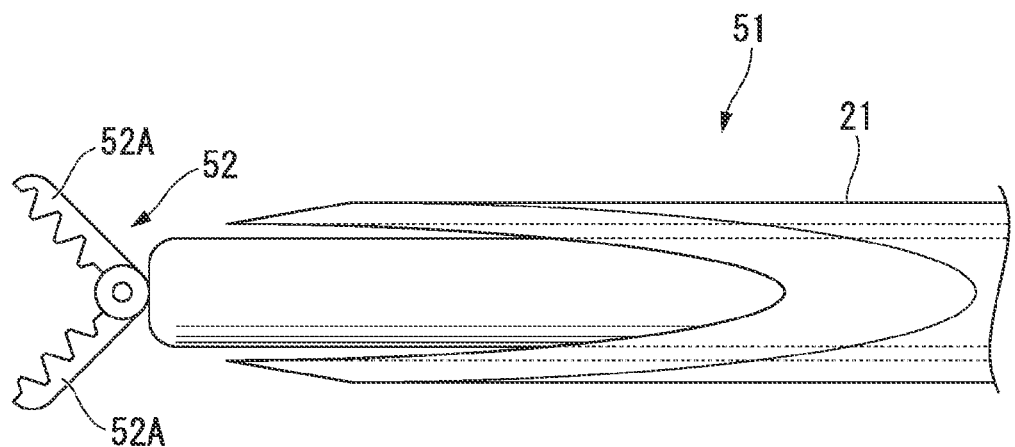
FIG. 18 is a partially enlarged view showing the distal end portion of the medical instrument of another modified example of the third embodiment of the present invention.
Figure 19:
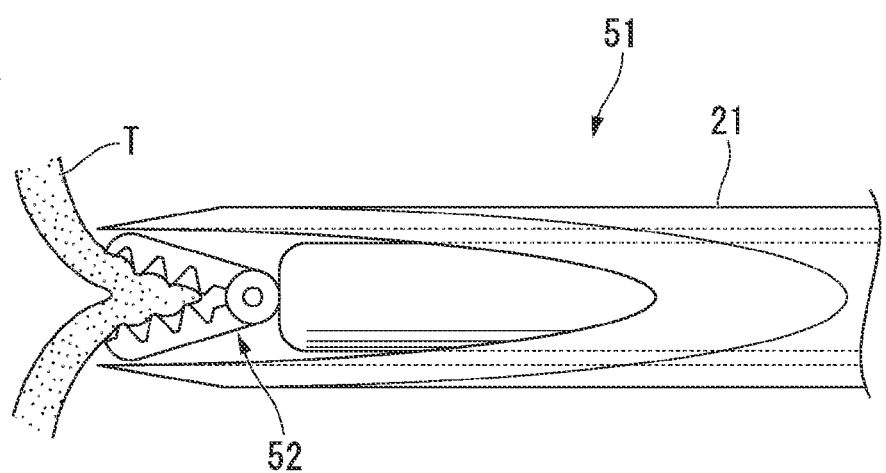
FIG. 19 is a view showing an operation at the time of using the medical instrument shown in FIG. 18.

In a medical instrument 51 of the modified example shown in FIG. 18, as the tissue-supporting member, a pair of forceps 52 including a pair of forceps blades 52A is inserted into the cutting blade member 21. The forceps 52 can open and close the pair of forceps blades 52A by moving forward and backward an operation member (not shown) such as an operation wire that has a known configuration and is connected to the forceps blades 52A in the axis direction by an operation portion (not shown) provided to the proximal end. In the medical instrument 51 having this configuration, it is also possible to prevent the tissue T from turning along with the turning operation of the cutting blade member 21 by holding the tissue T with the forceps 52 as shown in FIG. 19. As described so far, a tissue-holding portion is not particularly limited in terms of the specific configuration as long as this portion can inhibit the tissue T from turning together as described above.

Figure 20:
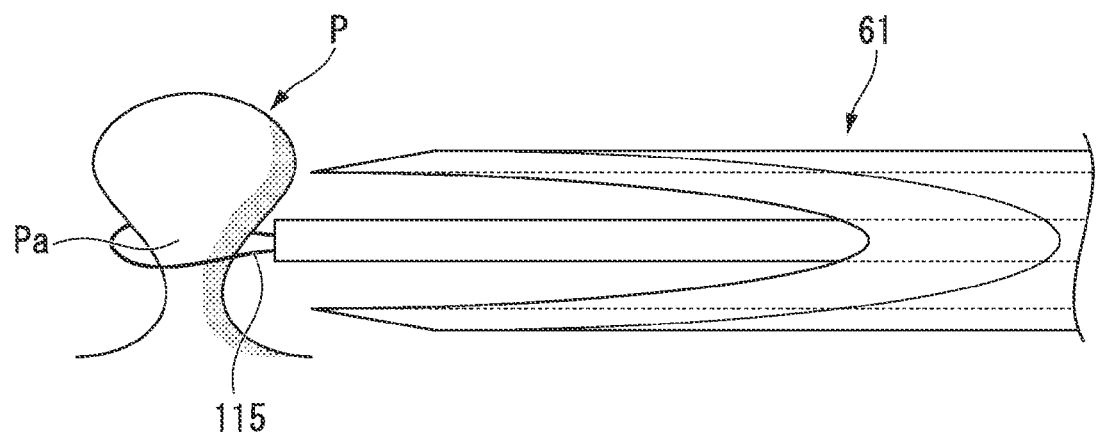
FIG. 20 is a view showing the medical instrument of the other modified example of the third embodiment of the present invention.

In addition, although a hole is not formed, when a neck portion Pa of a polyp P is excised by a medical instrument 61 of the modified example as shown in FIG. 20, a snare wire 115 or the like may be used as the tissue-supporting member.

The medical needle and the medical instrument (hereinbelow, referred to as "the medical needle and instrument" in general) according to the embodiment of the present invention can be used for various procedures performed on various body tissues. Hereinbelow, procedures to which the medical needle and instrument can be applied and the outline of the applicable procedures will be described.

The first applicable procedure is various types of drainage such as drainage of pus. Herein, a pancreatic cyst will be described for example.

The pancreatic cyst is a cyst formed in the pancreatic parenchyma. Herein, a case in which a cyst 105 is formed at the site shown in FIG. 21 will be described for example.

Figure 21:
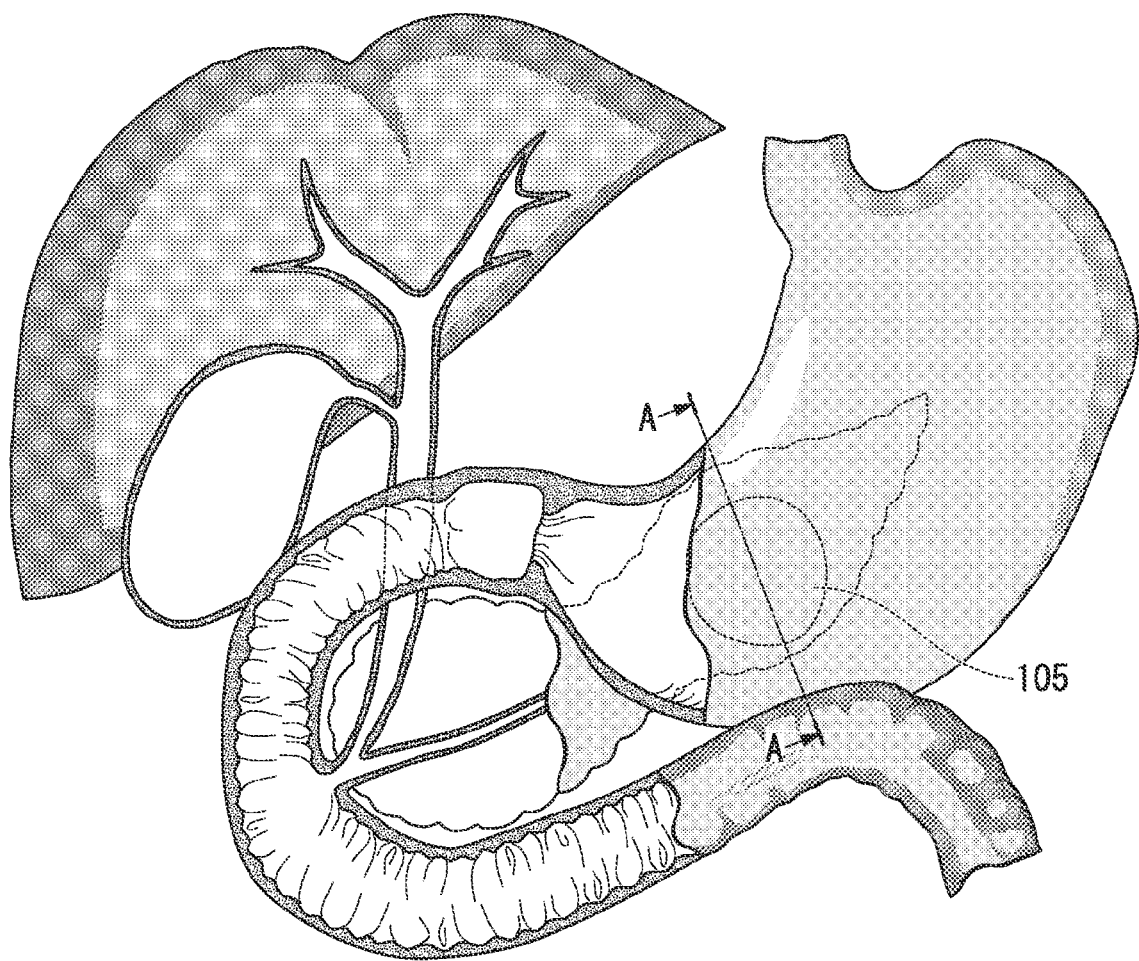
FIG. 21 is a view showing an example in which the medical needle and the like according to the embodiment of the present invention are applied to a procedure performed on a pancreatic cyst.
Figure 22:
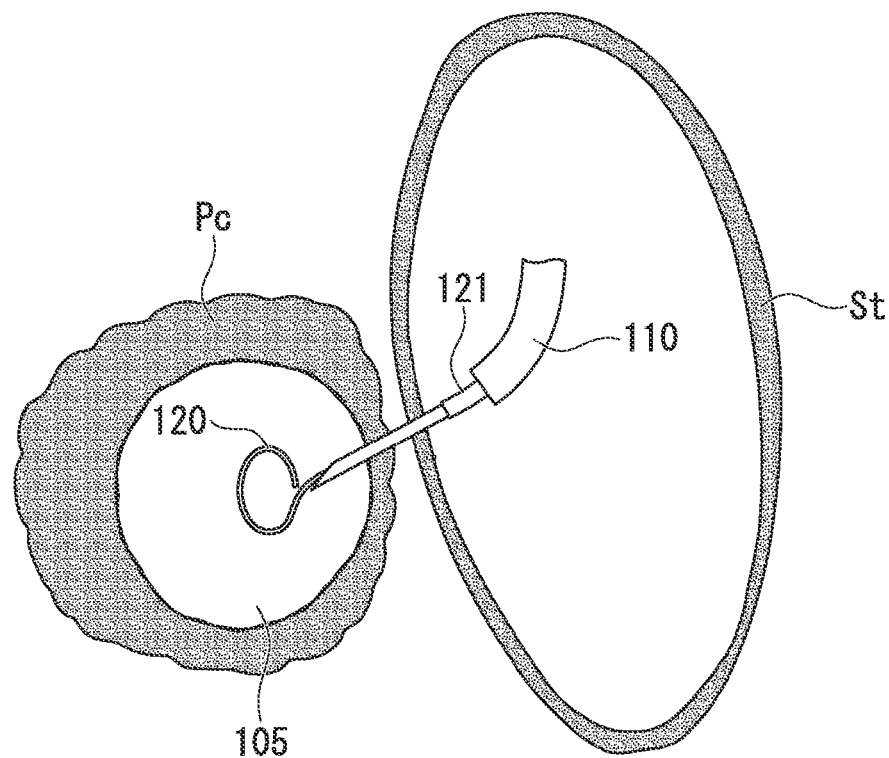
FIG. 22 is a view showing a process of the method of the procedure performed on the pancreatic cyst in a cross-section taken along the line A-A of FIG. 21.
Figure 23:
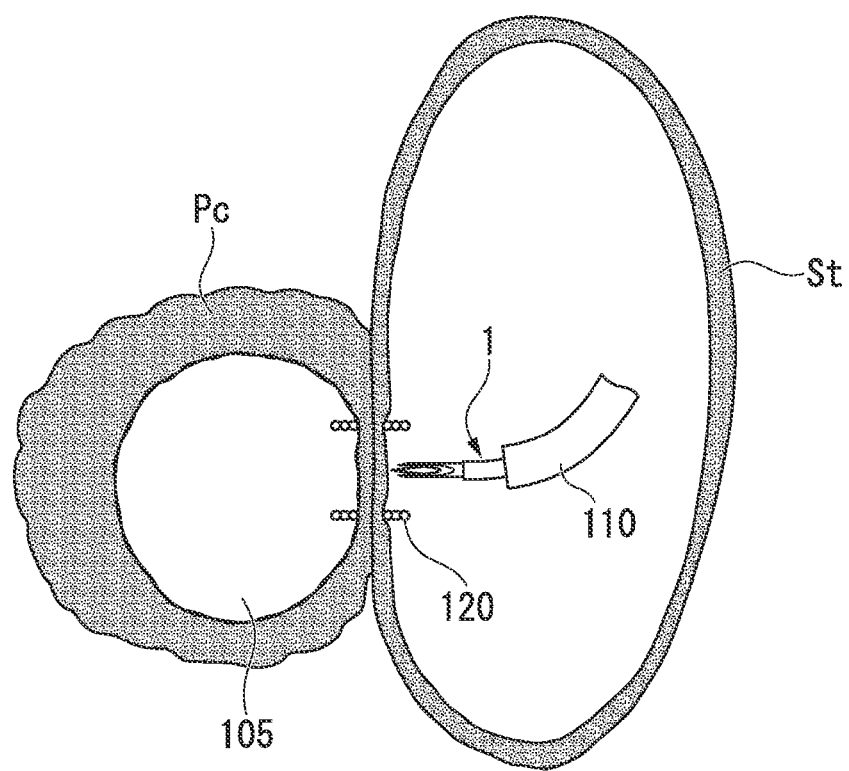
FIG. 23 is a view showing a process of the method of the procedure performed on the pancreatic cyst in the cross-section taken along the line A-A of FIG. 21.

Both FIGS. 22 and 23 are views showing the process of the method of a procedure performed on the pancreatic cyst in the cross-section taken along the line A-A of FIG. 21.

First, the operator inserts an endoscope 110 into the stomach St. The endoscope to be used is not particularly limited, and a straight-view endoscope, a side-view endoscope, an oblique-view endoscope, and the like may be appropriately selected. The operator then inserts an applicator 121 loaded with a coil-like tissue fastening tool 120 into a channel (not shown) of the endoscope 110, and causes the applicator 121 to protrude from the distal end of the endoscope 110. Thereafter, while checking the position of the cyst 105 by using an ultrasonic image, an X-ray fluoroscopic image, a CT image, and the like (hereinbelow, referred to as "an ultrasonic image and the like" in general), the operator makes the distal end of the applicator 121 puncture the stomach wall, and causes the distal end of the applicator 121 to penetrate the stomach wall and pancreas Pc and protrude to the inside of the cyst 105 as shown in FIG. 22.

Subsequently, the operator pushes the tissue fastening tool 120 from the applicator 121 and places, and tightly fixes the pancreas Pc to the stomach St as shown in FIG. 23. At this time, the inner wall of the cyst 105 has been hardened far more than the general pancreatic parenchyma due to fibrosis or the like, so it is possible to reliably fix the pancreas by the tissue fastening tool 120. As the tissue fastening tool 120 and the applicator 121, for example, it is possible to use the tissue fastening tool and the applicator disclosed in the specification of US Patent Application Publication No. 2008/0208214.

After placing of the tissue fastening tool 120, the operator pulls out the applicator 121, and inserts the medical needle 1 and the instrument (indicated as the medical needle 1 and the like herein) according to the embodiment of the present invention into a channel of the endoscope 110 and causes the medical needle 1 and the like to protrude from the distal end.

When the medical needle 1 and the like are inserted into the channel of the endoscope, if a stylet 122 or the like that has a curved surface at a distal end 122A as shown in FIG. 12 is inserted into the lumen, and the medical needle 1 and the like are delivered while the distal end 122A is caused to protrude further than the medical needle 1 and the like, it is possible to prevent the inner wall of the channel from being damaged due to the projection of the medical needle and the like.

In this procedure, if an ultrasonic image is used as means for checking, the applicator 121 or the medical needle 1 and the like may be introduced using an ultrasonic endoscope so as to check using the image of the ultrasonic endoscope.

After the distal end of the medical needle or the like is caused to protrude into the stomach St, the operator makes the medical needle 1 or the like puncture the tissue such that the medical needle 1 or the like penetrates the tissue surrounded by the tissue fastening tool 120 while checking the position of the distal end by using the ultrasonic image and the like, and forms a circular hole by performing the turning operation. After the hole is formed, the medical needle 1 or the like is pulled out of the endoscope 110, and a series of procedures ends. The approximately circular hole formed by the medical needle 1 and the like is not easily obstructed, and the contents of the cyst 105 are reliably drained through this hole.

The second applicable procedure is anastomosis or connection of luminal tissues performed by fistulization. These procedures can be performed suitably by combining the medical needle and the like with the tissue fastening tool 120, the applicator 121, and the like described above.

Figure 24:
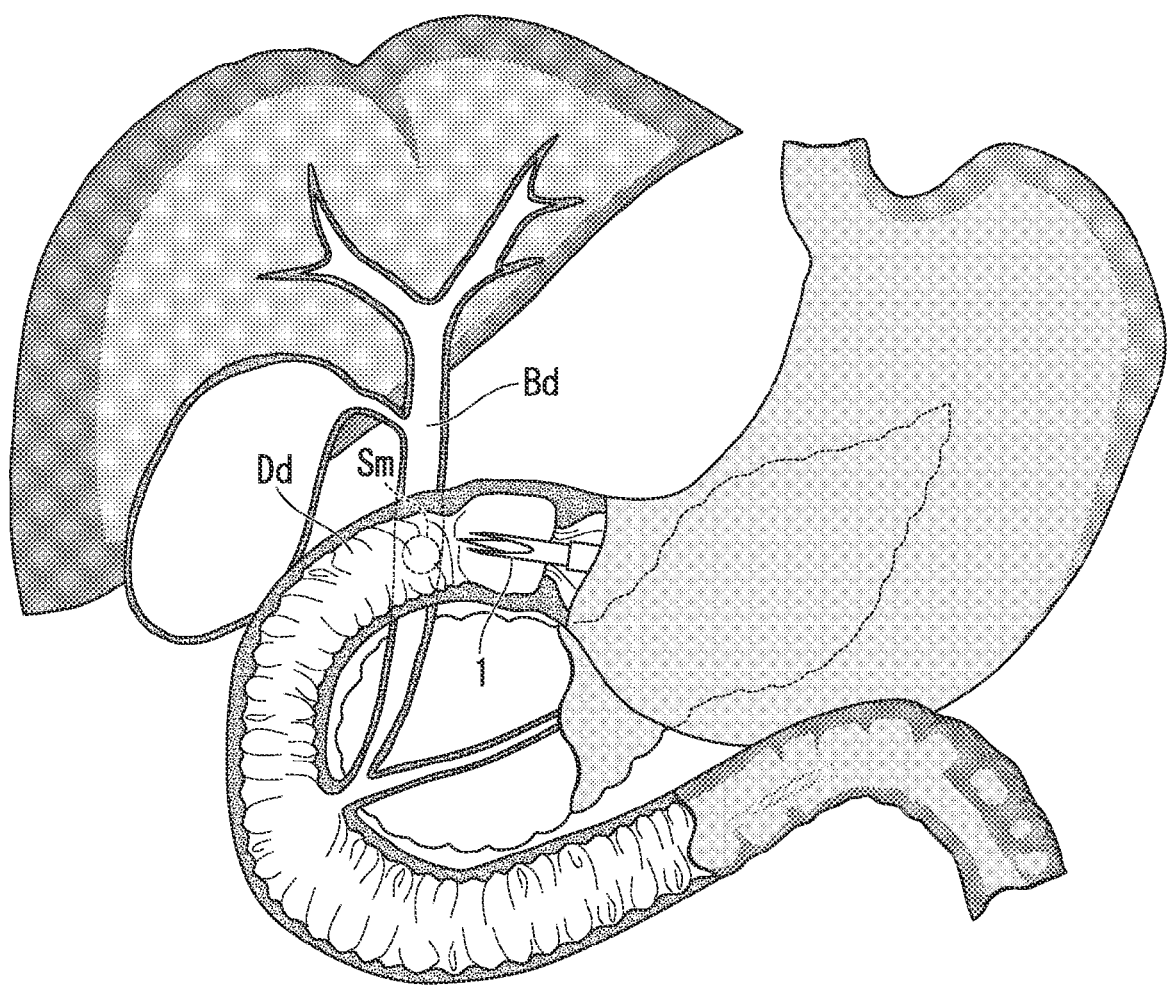
FIG. 24 is a view showing an example in which the bile duct is connected to the duodenum by using a medical needle system according to the embodiment of the present invention.
Figure 25:
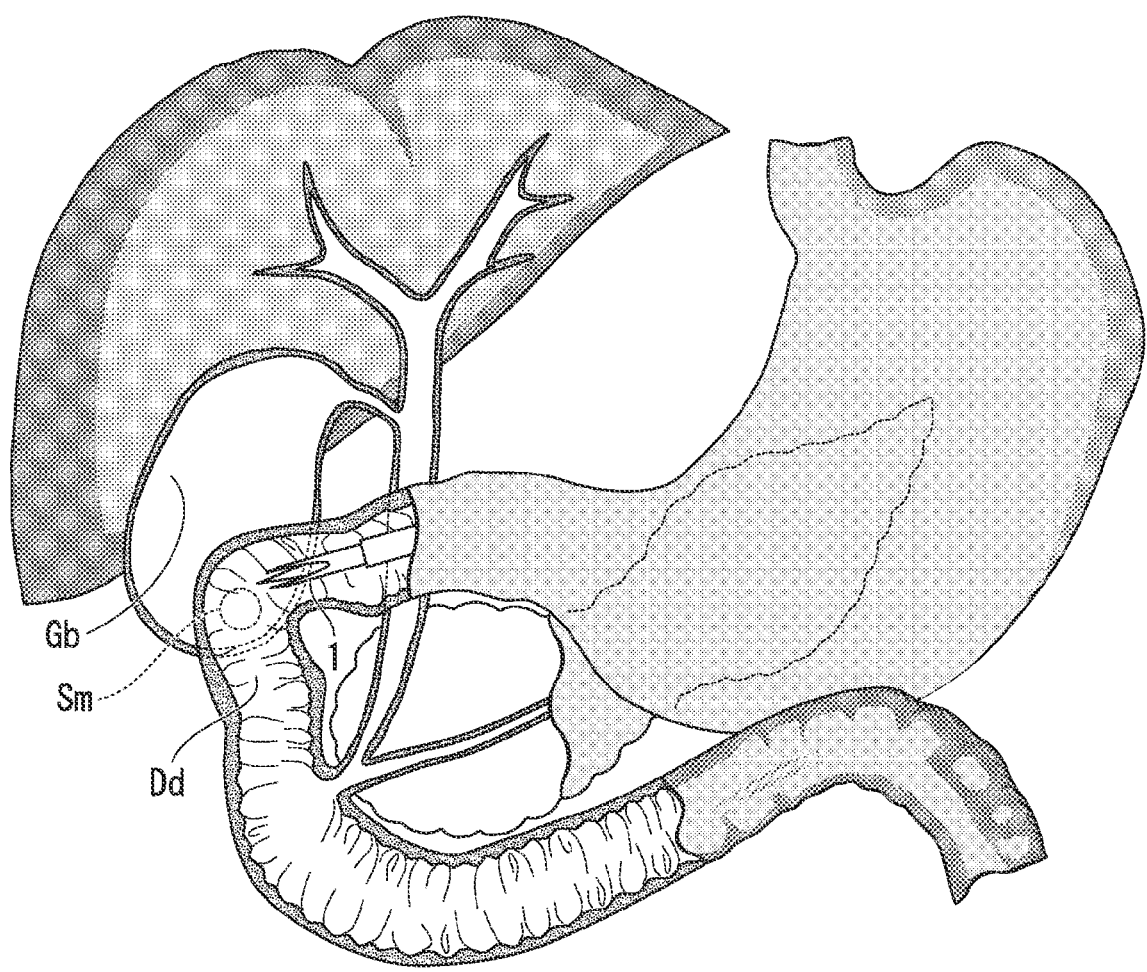
FIG. 25 is a view showing an example in which the gall bladder is connected to the duodenum by using the medical needle system according to the embodiment of the present invention.

Examples of the luminal tissues connected by fistulization include the bile duct Bd and the duodenum Dd shown in FIG. 24, the gall bladder Gb and the duodenum Dd shown in FIG. 25, and the like. In the case of these structures, a fistula is formed in the site indicated by a symbol Sm in the same process as described above by using the medical needle 1 and the like, whereby it is possible to reliably drain the bile that is not easily drained due to biliary obstruction or gallstones or to perform various procedures on tumors and the like by forming an access route into the biliary tract.

Figure 26:
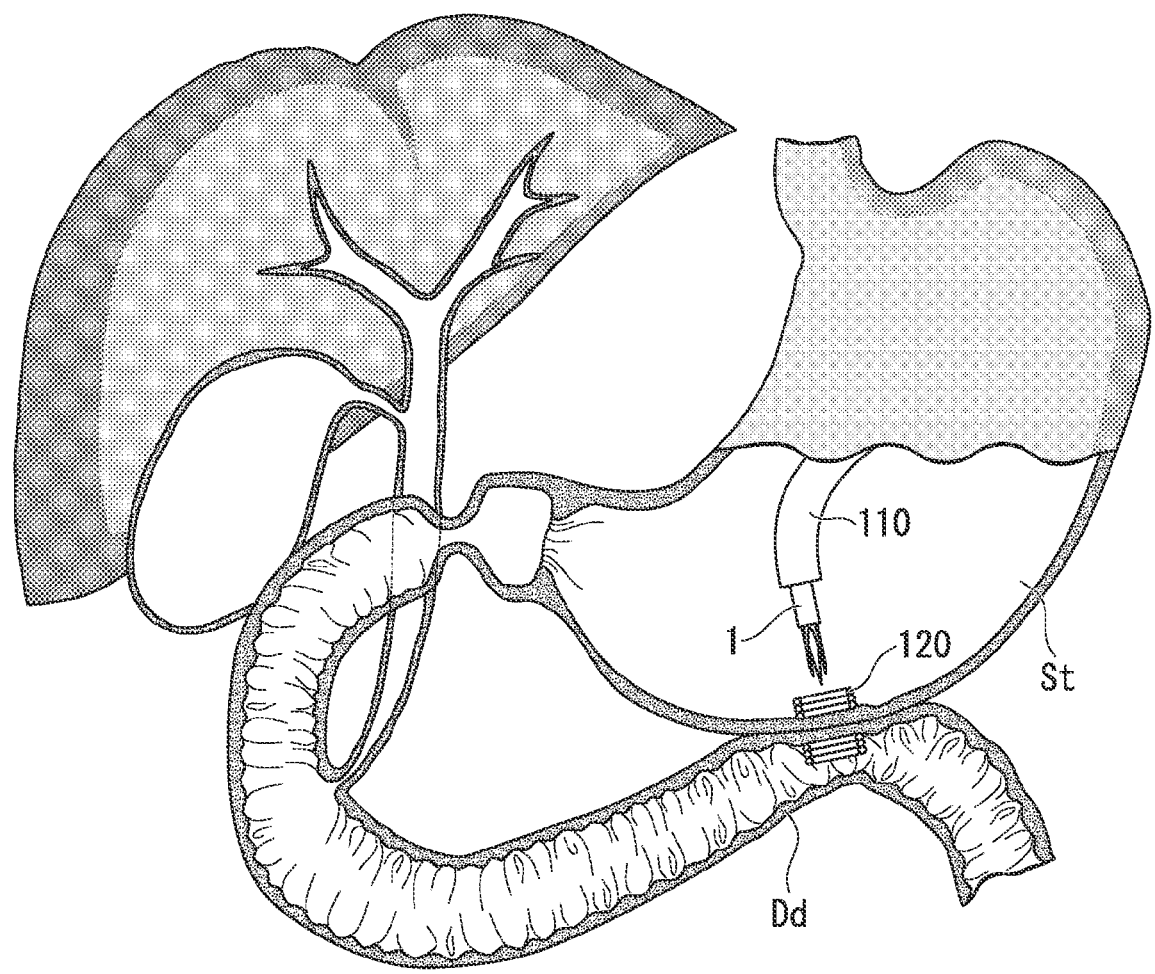
FIG. 26 is a view showing an example in which the stomach is connected to the duodenum by using the medical needle system according to the embodiment of the present invention.

In addition, the medical needle and the like according to the embodiment of the present invention can be applied to the anastomosis of the stomach St and the duodenum Dd as shown in FIG. 26; alternatively, they can also be applied to the anastomosis of alimentary tracts such as the large intestine and ileum, angiostomy, or the like, though these procedures are omitted in the drawing. Examples of applicable diseases include ileus, alimentary tract obstruction caused by various malignant tumors, and the like.

With the medical needle used in the related art, a slit-like hole is formed by puncturing. Accordingly, in the procedure of connection or anastomosis as described above, an additional procedure such as expanding the formed hole with a balloon is required in some cases. However, the hole formed by the medical needle and the like according to the embodiment of the present invention does not practically require such an additional procedure, and steps of the procedure can be simplified.

In addition, in these procedures, the luminal tissue is unstable without being supported by another tissue in many cases. Therefore, compared to the medical needle according to the embodiment of the present invention, a medical instrument that can reliably support the luminal tissue by the tissue-supporting member is more suitable.

The third applicable procedure is forming markings in a tissue.

Figure 27:
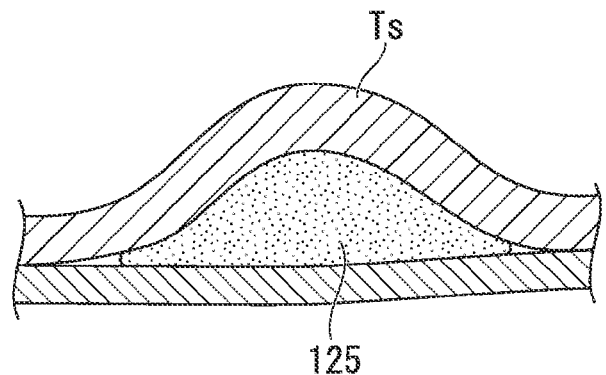
FIG. 27 is a view showing an example in which marking is performed on a tissue by using the medical needle system according to the embodiment of the present invention.
Figure 28:
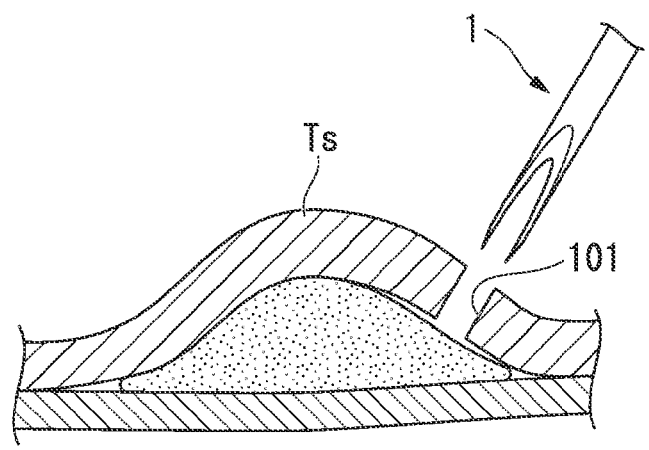
FIG. 28 is a view showing an example in which marking is performed on a tissue by using the medical needle system according to the embodiment of the present invention.
Figure 29:
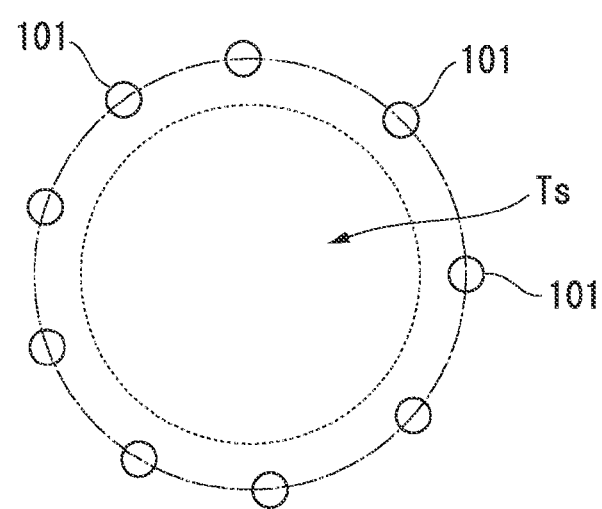
FIG. 29 is a view showing an example in which marking is performed on a tissue by using the medical needle system according to the embodiment of the present invention.

FIGS. 27 to 29 show the flow of the procedure of ESD (endoscopic submucosal dissection) as an example of forming markings by using the medical needle and the like. A bulging agent 125 is injected into a lower portion of a tissue Ts to be excised as shown in FIG. 27 by a known process, and then plural holes 101 are formed as markings around the tissue Ts in a plan view by using the medical needle 1 and the like as shown in FIGS. 28 and 29. The holes 101 function as markings and penetrate the tissue Ts. Therefore, the operator can easily excise the tissue Ts by making plural small incisions by using a high-frequency knife so as to connect the plural holes 101 (indicated as a dashed line in FIG. 29).

Figure 30:
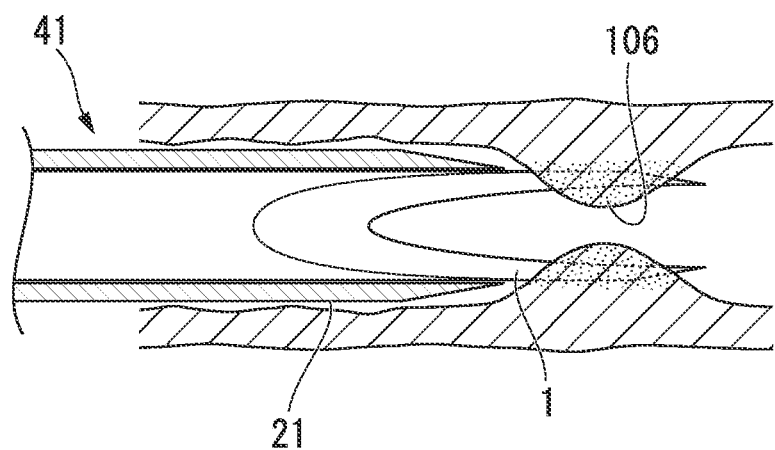
FIG. 30 is a view showing an example in which atherectomy is performed in a blood vessel by using the medical needle system of the present invention.

The fourth applicable procedure is atherectomy or the like performed in the blood vessel wall. As shown in FIG. 30, the medical needle 1 and the like are introduced to a site in which the blood vessel wall is thickened to cause stenosis due to an atheroma 106, calcification, or the like by using a catheter or the like. When the atheroma 106 or the like is removed, the medical needle 1 and the like (for example, the medical instrument 41 including an inner needle (tissue-supporting member 1) and an outer needle (the cutting blade member 21)) are used under X-rays. Accordingly, if trying to puncture the outer needle first and then operate the inner needle, the operator cannot see the movement of the inner needle under X-rays, so the inner needle is made to puncture the tissue first.

Figure 31:
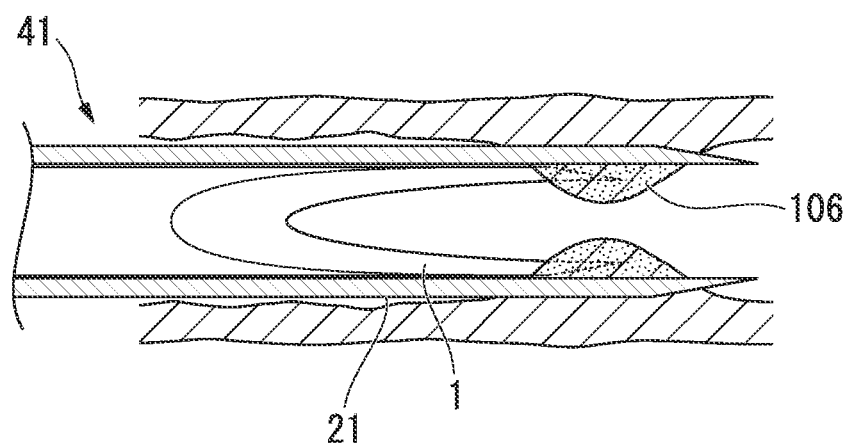
FIG. 31 is a view showing an example in which atherectomy is performed in a blood vessel by using the medical needle system according to the embodiment of the present invention.

Subsequently, as shown in FIG. 31, if the turning operation is performed while the outer needle (the cutting blade member 21 or the like) penetrates the atheroma 106 or the like, it is possible to widen the lumen by removing the atheroma 106 or the like. Since the excised atheroma or the like induces thrombosis in some cases, it is preferable to recover the atheroma to the inside of the medical needle 1 and the like by suction or the like.

Figure 32:
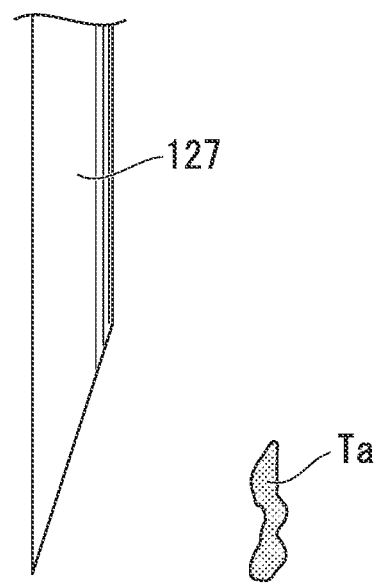
FIG. 32 is a view showing an example of a medical needle used in the related art and a tissue fragment collected by this medical needle.

The fifth applicable procedure is biopsy. With the medical needle used in the related art, a slit-like hole is formed in a tissue, but the tissue is not actively excised. Consequently, as shown in FIG. 32, a collected tissue fragment Ta is small in many cases. Therefore, in order to collect a sufficient amount of tissue with a medical needle 127 used in the related art, it is necessary to perform puncturing a plurality of times or to be skilled in the procedure.

Figure 33:
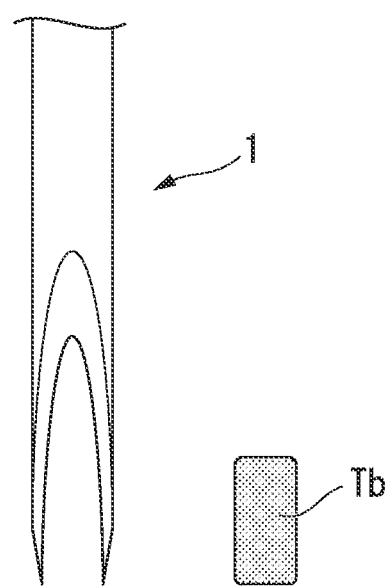
FIG. 33 is a view showing an example of the medical needle system according to the embodiment of the present invention and a tissue fragment collected by this medical needle system.

If the medical needle 1 and the like according to the embodiment of the present invention are used, it is possible to excise a tissue so as to hollow out the tissue. Accordingly, even if the dimensions of the needle are the same as that of the medical needle 127 used in the related art, it is possible to collect an approximately cylindrical tissue Tb that includes more cells than the tissue fragment Ta does, as shown in FIG. 33. Consequently, a larger amount of tissue can be collected without requiring skillfulness, and it is possible to lighten the burden on a patient by reducing the number of times a tissue is punctured.

The target tissue of biopsy is not particularly limited, and the medical needle and the like according to the embodiment of the present invention can be applied to various tissues punctured for biopsy, such as a liver, pancreas, mammary gland, prostate, and kidney. In addition, similarly to the case of atherectomy or the like, the collected tissue may be recovered into the lumen of the medical needle and the like by suction or the like.

Figure 34:
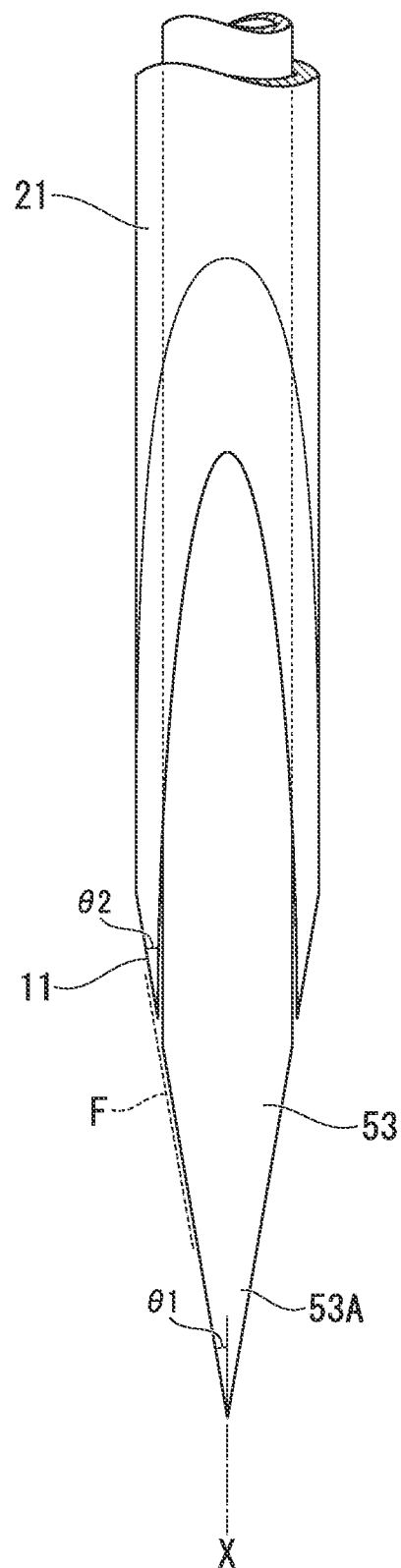
FIG. 34 is a view showing an example illustrating how the medical needle and the tissue-penetrating portion of the present invention are combined when the medical needle according to the embodiment of the present invention is used for biopsy.

For biopsy, the medical needle according to the embodiment of the present invention may be used in combination with a needle member (tissue-penetrating portion) 53 as shown in FIG. 34. The needle member 53 has one projection 53A that protrudes in an approximately conical shape at the distal end, as a general trocar.

A procedure using the medical needle in combination with the needle member 53 will be described using a case of combining the medical needle 21 with the needle member 53 for example. This procedure is effective for, for example, a case where another tissue in which an approximately circular hole is not desired to be formed is positioned in front of the target tissue of biopsy, similarly to pancreatic biopsy performed by a transgastric approach.

Figure 35:
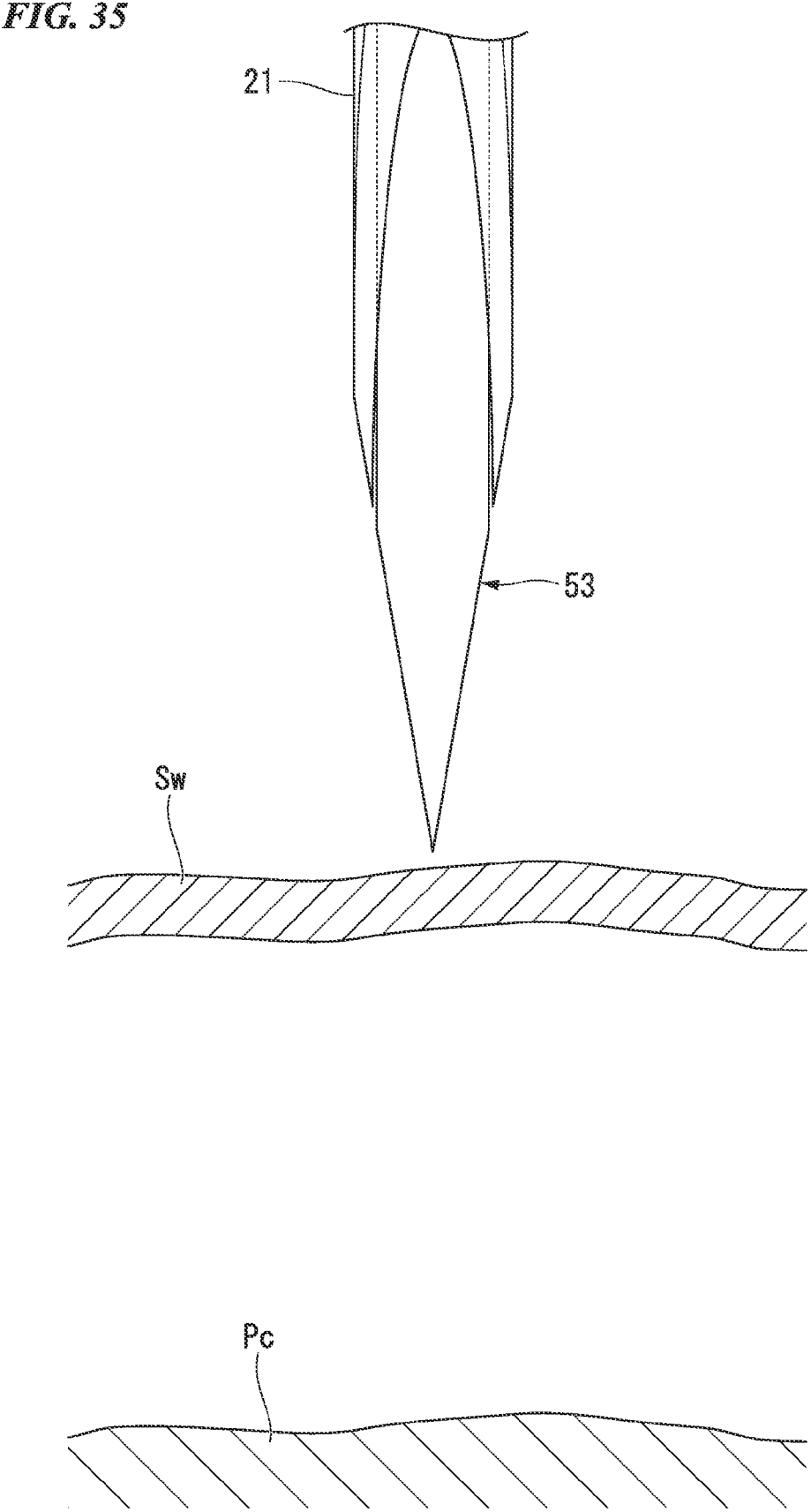
FIG. 35 is a view showing an example of a biopsy procedure using the combination of the medical needle and the tissue-penetrating portion according to the embodiment of the present invention.

First, the operator delivers the needle member 53 into the stomach while the needle member 53 is being inserted into the lumen of the medical needle 21 as shown in FIGS. 34 and 35, and causes the distal end of the needle member 53 to protrude from the distal end of the medical needle 21. In this state, the operator causes a stomach wall Sw to be penetrated. Having one projection 53A at the distal end, the needle member 53 can penetrate the stomach wall Sw with relatively little force. At this time, as the needle member, if a member of which a taper angle $\theta 1$ of the distal end is approximately the same as a taper angle $\theta 2$ of the puncturing portion 11 of the medical needle 21 is used as shown in FIG. 34, a surface F that smoothly continues consistently from the medical needle 21 to the needle member 53 is formed at the distal end, so it is possible to make the needle smoothly puncture a tissue such as the stomach wall Sw.

Figure 36:
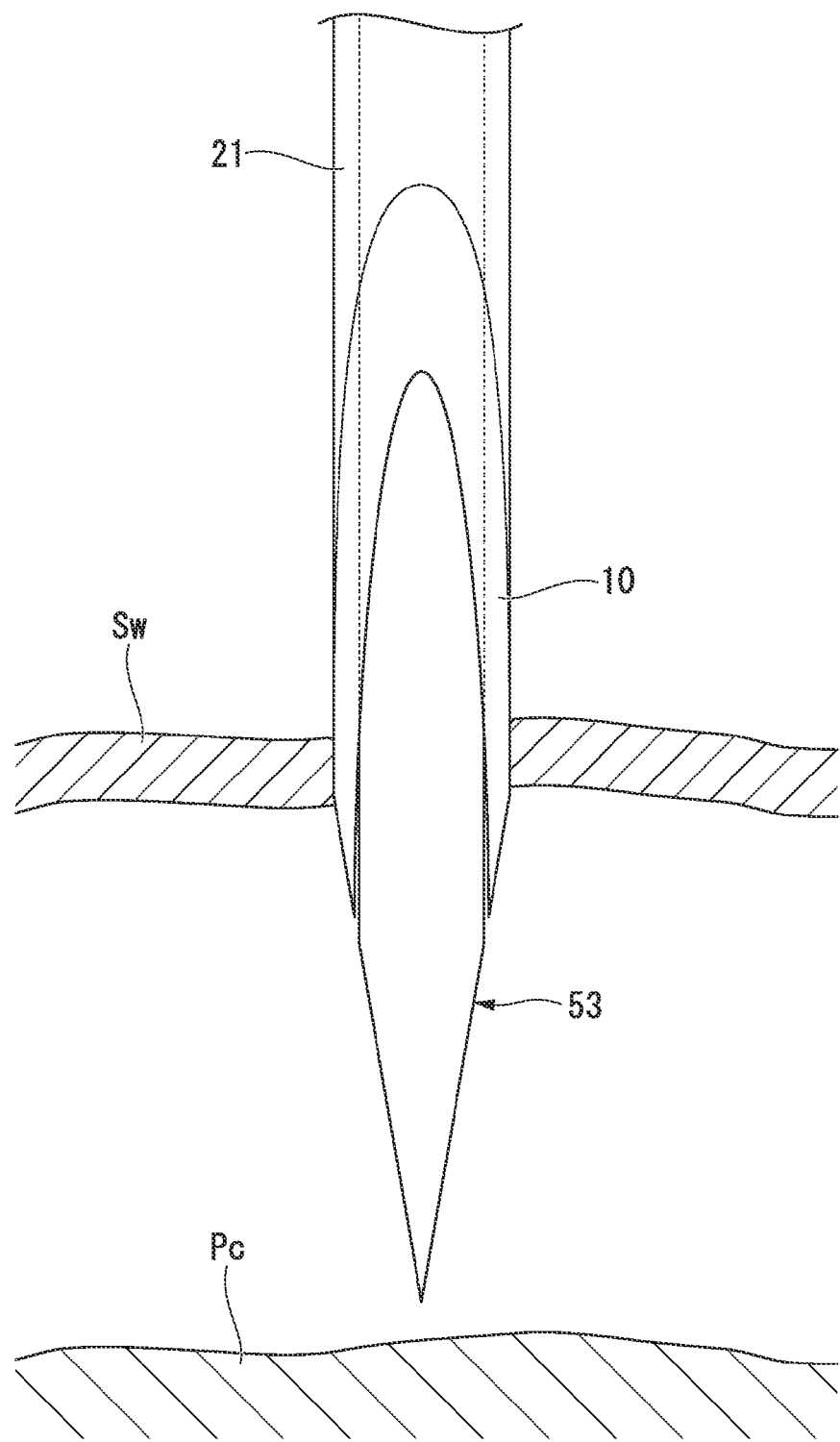
FIG. 36 is a view showing an example of the biopsy procedure using the combination of the medical needle and the tissue-penetrating portion according to the embodiment of the present invention.
Figure 37:
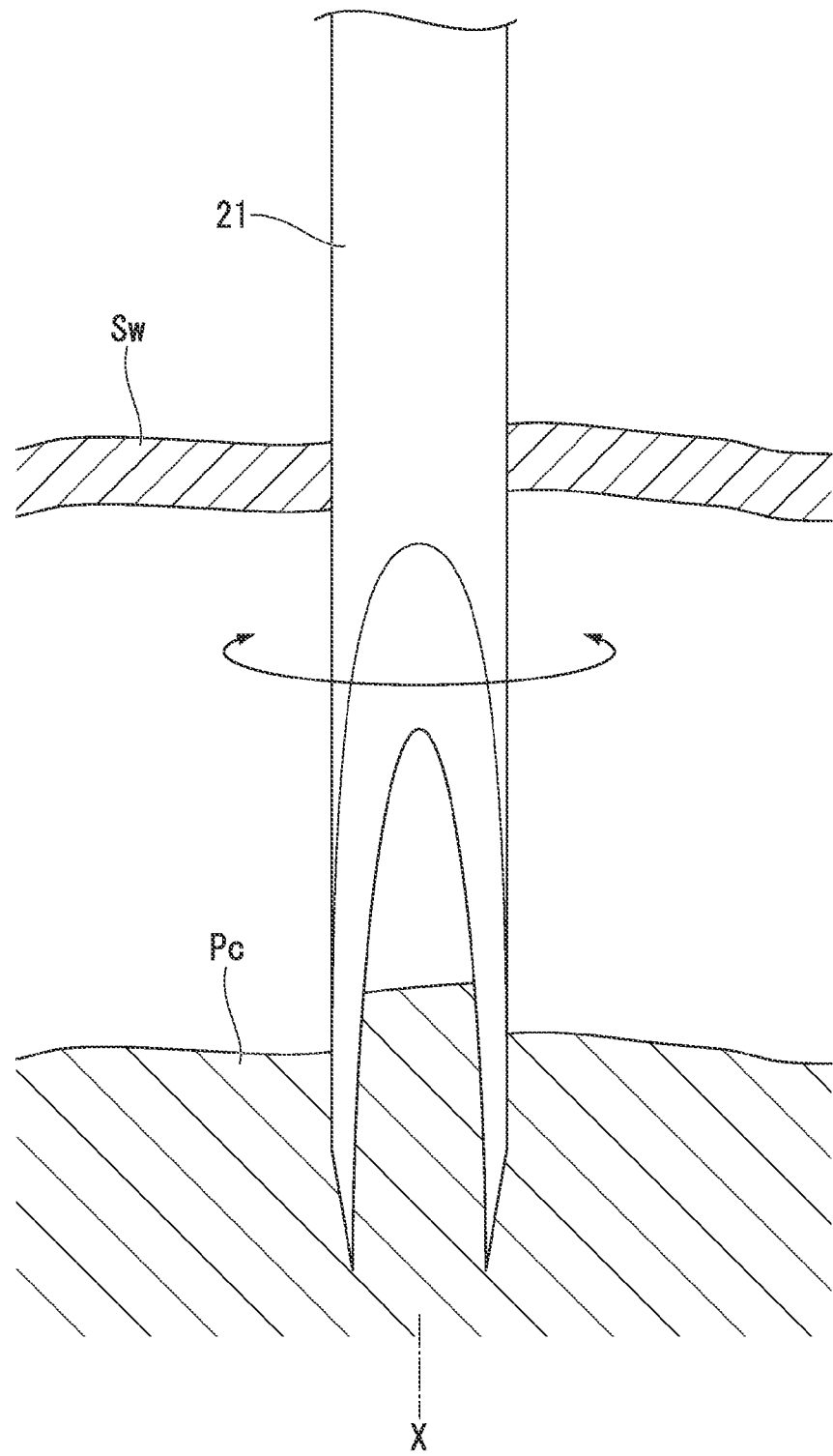
FIG. 37 is a view showing an example of the biopsy procedure using the combination of the medical needle and the tissue-penetrating portion according to the embodiment of the present invention.

As shown in FIG. 36, when the medical needle 21 penetrates the stomach wall Sw, the operator pulls the needle member 53 out of the medical needle 21, and makes the projection 10 of the medical needle 21 puncture the pancreas Pc. Subsequently, as shown in FIG. 37, the operator turns the medical needle 21 on the axis X, thereby excising and recovering a portion of the pancreas Pc. Instead of pulling out the needle member 53, the operator may move the needle member 53 backward relative to the medical needle 21 to such a degree that the collection of the tissue is not hindered.

In the procedure described so far, the stomach wall Sw is penetrated with the needle member 53 having one projection 53A. In addition, when the medical needle 21 is turned, since the projection 10 is separated from the stomach wall Sw, the tissue of the stomach wall Sw is excised by the medical needle 21. That is, only a slit-like hole is opened in the stomach wall Sw, and an approximately circular hole from which the tissue is hollowed out is not formed. Consequently, while a large amount of tissue is collected from the pancreas Pc by the method used in the related art, the stomach wall tissue after the tissue collection is rapidly repaired, so it is possible to reduce the invasiveness of a procedure.

Figure 38A:
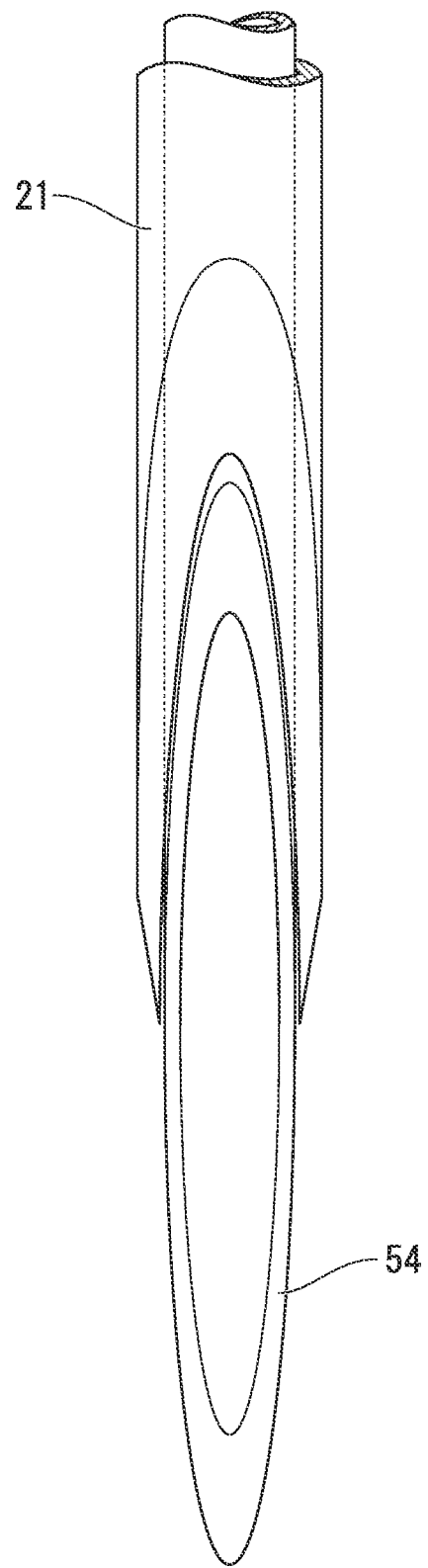
FIG. 38A is a front view showing another example of the combination of the medical needle and the tissue-penetrating portion according to the embodiment of the present invention.
Figure 38B:
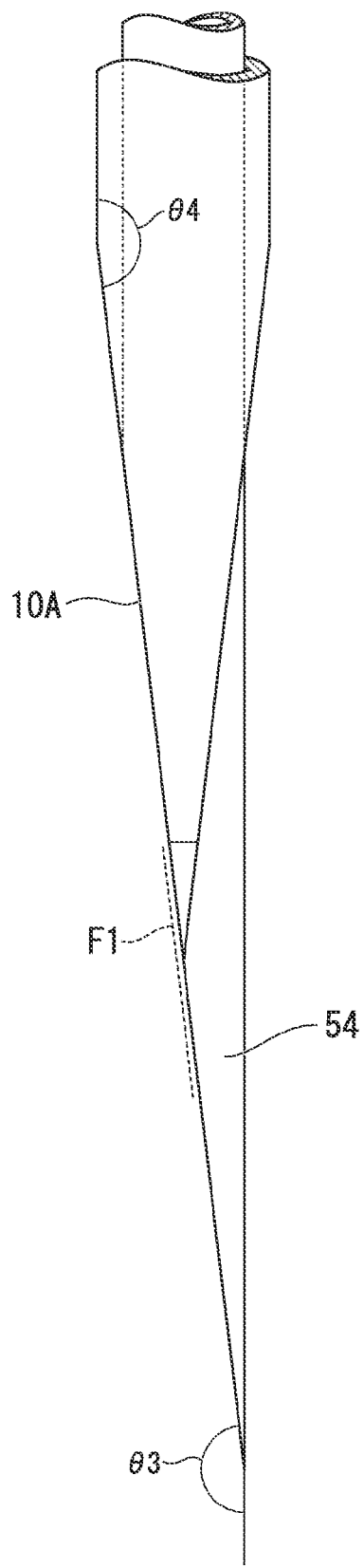
FIG. 38B is a side view showing the other example of the combination of the medical needle and the tissue-penetrating portion according to the embodiment of the present invention.

In the above procedure, the tissue-penetrating portion to be combined with the medical needle is not limited to a member that has a shape of a distal end as the needle member 53. For example, as shown in FIGS. 38A and 38B, an injection needle 54 which is used in the related art and can be easily made to puncture a tissue may be used as the tissue-penetrating portion. When the tissue-penetrating portion that has a shape of a distal end asymmetric to its own central axis as the injection needle 54 is combined, a supplementary angle $\theta 3$ of the distal end may be set to the same as an angle $\theta 4$ which is formed between the outer circumferential surface of the medical needle 21 and the slope 10A for forming a projection 10. In this case, by forming a surface F1 that continues smoothly similarly to the surface F described above at the distal end, it is possible to smoothly penetrate the tissue.

In various procedures other than biopsy, when a non-target tissue in which a hole is not desired to be formed is positioned in front of a target tissue in which a hole is desired to be formed, if the medical instrument and the tissue-penetrating portion according to the embodiment of the present invention are combined, the same effect is obtained. In this case, preferably, the operator first pulls out the tissue-supporting member of the medical instrument, inserts the tissue-penetrating portion, causes the distal end of this portion to protrude so as to penetrate a non-target tissue, and then changes again the tissue-penetrating portion to the tissue-supporting member to perform a procedure on a target tissue.

Examples of the non-target tissue include various alimentary tract walls such as a large intestine wall, a duodenum wall, and an esophagus wall, and the like, in addition to the stomach wall described above.

As described above, the medical needle according to the embodiment of the present invention requires greater puncturing force compared to a general injection needle. Therefore, the tissue-penetrating portion may be caused to penetrate only when the needle is made to puncture a tissue such that the tissue-penetrating portion is used for assisting the needle to puncture the tissue.

So far, various embodiments of the present invention and applicable procedures have been described, but the present invention is not limited to the examples. Within a range that does not depart from the scope of the present invention, configurational addition, omission, substitution, and other modifications can be made.

For example, in the medical needle and the like according to the exemplary embodiment of the present invention, a parameter such as rigidity, length, or the like may be set appropriately according to the target tissue, the access route, or the like.

For example, when introduced through a channel of an endoscope, the medical needle and the like are preferably formed so as to have flexibility of such a degree that the medical needle and the like can smoothly move forward and backward in the meandering channel and so as to be longer than the channel. At this time, only the distal end portion puncturing a tissue may be formed of a metal or the like, and the remaining portion may be formed of a tube or the like including a resin or the like that has a certain rigidity.

On the other hand, when the medical needle and the like are caused to directly approach a target tissue from the outside of the body similarly to liver biopsy, a hard needle or medical instrument that always stays straight may be used.

When an operator performs a procedure while checking the distal end of the medical needle and the like by using an ultrasonic image, the outer circumferential surface of the medical needle and the like may be surface-treated to improve visibility with respect to ultrasonic waves. Examples of the surface treatment include forming dimples, forming micro-grooves by a knurling process, and the like. In addition, the micro-grooves may be formed spirally so as to make it possible to visually check the turning operation performed. When the surface-treated medical needle and the like are produced, it is preferable to prepare in advance a tubular member having undergone a desired surface treatment and perform a process for forming projections or edge portions on the member.

As the material of the medical needle or the medical instrument of the present invention, a hyperelastic pipe or the like formed of a shape-memory alloy may be used in addition to the stainless steel or the like described above. The inner surface of these tubular members may be processed to be a mirror surface.

So far, preferable examples of the present invention have been described, but the present invention is not limited to these examples. Within a range that does not depart from the scope of the present invention, configurational addition, omission, substitution, and other modifications can be made. The present invention is limited not to the above description but only to the claims attached.

The invention claimed is:

1. A medical instrument comprising:
   a cutting instrument in which a lumen is formed along a longitudinal axis, the cutting instrument having an opening portion which is formed at a distal end of the cutting instrument and communicates with the lumen, the cutting instrument having a cutting blade portion which is formed in a periphery of the opening portion and which is configured to cut a tissue in a circumferential direction of the cutting instrument, and
   an engaging needle which is provided at an inside of the cutting instrument, the engaging needle having a distal opening which opens at the distal end of an inner space formed around a central axis of the engaging needle, the distal opening being configured to cut into the tissue such that the tissue is capable of entering into the inner space through the distal opening, wherein
   the engaging needle comprises:
   a first engaging projection which has a sharpened shape at a distal end of the engaging needle in a direction extending toward the distal end of the cutting instrument from a proximal end of the cutting instrument, the first engaging projection being configured to be capable of engaging the tissue; and
   a second engaging projection which has a sharpened shape at the distal end of the engaging needle in the direction extending toward the distal end of the cutting instrument from the proximal end of the cutting instrument, the second engaging projection being arranged at a position apart from the first engaging projection in a circumferential direction of the distal end of the engaging needle, the second engaging projection being configured to be capable of engaging puncture the tissue; wherein
   the cutting instrument being rotatable with respect to both the first engaging projection and the second engaging projection, the cutting instrument being movable along the longitudinal axis with respect to both the first engaging projection and the second engaging projection,
   the cutting instrument is configured to make an incision in the tissue by cutting the tissue in the circumferential direction of the cutting instrument in a state in which both the first engaging projection and the second engaging projection straightly puncture the tissue, which is positioned in a cutting line for making the incision in accordance with an advance of the first engaging projection and the second engaging projection with respect to the cutting instrument;
   the cutting blade portion is positioned outward in a radial direction of the distal opening from a periphery of the distal opening of the engaging needle,
   both the first engaging projection and the second engaging projection are formed radially offset from the distal opening and both the first engaging projection and the second engaging projection are arranged at a position on a side of a periphery of the opening portion of the cutting instrument radially offset from the cutting instrument;
   the first and second engaging projections are coupled at their proximal ends to a base, wherein the first and second engaging projections are fixed relative to the base;
   wherein the cutting blade portion has a first projection and a second projection sharply protruding in a direction extending along the longitudinal axis, the first engaging projection configured to be positioned between the first projection and the central axis of the engaging needle, the second engaging projection configured to be positioned between the second projection and the central axis of the engaging needle;

wherein the cutting blade portion of the cutting instrument is formed so as to incline with a first angle with respect to a tangent line of a circumference of an inner wall of the cutting instrument; each of the first engaging projection and the second engaging projection includes side parts which are formed substantially perpendicular to a tangent line of a circumference of an inner wall of the engaging needle and have a second angle between the tangent line of a circumference of an inner wall of the engaging needle and each of the side parts; and the second angle is larger than the first angle.

2. The medical instrument according to claim 1, wherein the cutting blade portion is formed so as to have an acute angle between a tangent line of the lumen and the cutting blade portion in at least one position of an end portion in a circumferential direction of the cutting blade portion.

3. The medical instrument according to claim 1, wherein an outer circumferential surface of a distal end portion of each of the first engaging projection and the second engaging projection is processed such that the distal end portion becomes thinned toward the distal end.

4. The medical instrument according to claim 1, wherein at least a portion of the lumen is formed more thinly compared to other portions so as to form a small inner diameter portion.

5. The medical instrument according to claim 1, wherein the engaging needle is arranged in a concentric pattern with respect to the cutting instrument.

6. The medical instrument according to claim 5, wherein the engaging needle has a distal opening portion which is connected to the inner space of the cylindrical shape, and the first engaging projection and the second engaging projection are formed in a periphery of the distal opening portion and are provided at a position opposite to each other with respect to a center axis of the engaging needle.

7. The medical instrument according to claim 1, wherein the engaging needle is provided so as to be capable of freely advancing into or retracting with respect to the lumen of the cutting instrument along the longitudinal axis.

8. The medical instrument according to claim 1, wherein outer circumferential surfaces of the first engaging projection and the second engaging projection become gradually smaller toward a distal end of the engaging needle.

9. The medical instrument according to claim 1, wherein a distal end portion of the first engaging projection and a distal end portion of the second engaging projection define a circumference around a center axis of the engaging needle, and the distal end portion of the first engaging projection faces the distal end portion of the second engaging projection, and wherein the distal end portion of the first engaging projection, the distal end portion of the second engaging projection, and the distal end portion of the cutting blade portion are arranged in a concentric pattern.

* * * * *